(12) United States Patent
Jackson

(10) Patent No.: US 8,257,396 B2
(45) Date of Patent: Sep. 4, 2012

(54) POLYAXIAL BONE SCREW WITH SHANK-RETAINER INSET CAPTURE

(76) Inventor: Roger P. Jackson, Prairie Village, KS (US)

( * ) Notice: Subject to any disclaimer, the term of this patent is extended or adjusted under 35 U.S.C. 154(b) by 1044 days.

(21) Appl. No.: 12/154,460

(22) Filed: May 23, 2008

(65) Prior Publication Data

US 2008/0234761 A1    Sep. 25, 2008

Related U.S. Application Data

(63) Continuation-in-part of application No. 10/818,555, filed on Apr. 5, 2004, now Pat. No. 8,052,724, which is a continuation of application No. 10/464,633, filed on Jun. 18, 2003, now Pat. No. 6,716,214, application No. 12/154,460, which is a continuation-in-part of application No. 11/140,343, filed on May 27, 2005, and a continuation-in-part of application No. 10/651,003, filed on Aug. 28, 2003, now Pat. No. 8,137,386.

(60) Provisional application No. 60/931,362, filed on May 23, 2007.

(51) Int. Cl.
*A61B 17/70* (2006.01)
(52) U.S. Cl. .................... 606/246; 606/266
(58) Field of Classification Search ............ 606/246, 606/266–270
See application file for complete search history.

(56) References Cited

U.S. PATENT DOCUMENTS

| | | | |
|---|---|---|---|
| 2,346,346 A | 4/1944 | Anderson | |
| 2,362,999 A | 11/1944 | Elmer | |
| 2,531,892 A | 11/1950 | Reese | |
| 2,813,450 A | 11/1957 | Dzus | |
| 3,013,244 A | 12/1961 | Rudy | |
| 4,033,139 A | 7/1977 | Frederick | |
| 4,759,672 A | 7/1988 | Nilsen et al. | |
| 4,790,297 A | 12/1988 | Luque | |
| 4,946,458 A | 8/1990 | Harms et al. | |
| 5,019,080 A | 5/1991 | Hemer | |
| 5,129,388 A | 7/1992 | Vignaud et al. | |
| 5,207,678 A | 5/1993 | Harms et al. | |
| 5,261,912 A | 11/1993 | Frigg | |
| 5,312,404 A | 5/1994 | Asher et al. | |

(Continued)

FOREIGN PATENT DOCUMENTS

DE    19507141    9/1996

(Continued)

OTHER PUBLICATIONS

*EBI Omega 21* Brochure, EBI Spine Systems, pub. 1999.

(Continued)

*Primary Examiner* — Paul Prebilic
(74) *Attorney, Agent, or Firm* — John C. McMahon

(57) ABSTRACT

A polyaxial bone screw assembly includes a threaded shank body member having an upper portion with an internal drive and, alternatively, a laterally extending alignment rib or fin. The bone screw assembly also includes a lockable receiver coupling member, an open retainer ring member having a slit or gap and a compression insert member. An inset conical or cylindrical surface on the shank upper portion frictionally engages a similarly shaped inner surface of the retainer ring. The receiver includes a restrictive lower opening that allows for uploading the shank upper portion and compressed retainer ring into the receiver cavity, but prevents passage of the retainer ring out of the receiver once the ring inner surface engages the conical surface of the shank upper portion.

2 Claims, 6 Drawing Sheets

U.S. PATENT DOCUMENTS

| | | |
|---|---|---|
| 5,360,431 A | 11/1994 | Puno et al. |
| 5,395,371 A | 3/1995 | Miller et al. |
| 5,429,639 A | 7/1995 | Judet |
| 5,443,467 A | 8/1995 | Biedermann et al. |
| 5,466,237 A | 11/1995 | Byrd, III et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,496,321 A | 3/1996 | Puno et al. |
| 5,554,157 A | 9/1996 | Errico et al. |
| 5,569,247 A | 10/1996 | Morrison |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,607,426 A | 3/1997 | Ralph et al. |
| 5,607,428 A * | 3/1997 | Lin .............................. 606/287 |
| 5,647,873 A | 7/1997 | Errico et al. |
| 5,669,911 A | 9/1997 | Errico et al. |
| 5,672,176 A | 9/1997 | Biedermann et al. |
| 5,681,319 A | 10/1997 | Biedermann et al. |
| 5,690,630 A | 11/1997 | Errico et al. |
| 5,716,356 A | 2/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,782,833 A | 7/1998 | Haider |
| 5,797,911 A | 8/1998 | Sherman et al. |
| 5,800,435 A | 9/1998 | Errico et al. |
| 5,817,094 A | 10/1998 | Errico et al. |
| 5,863,293 A | 1/1999 | Richelsoph |
| 5,873,878 A | 2/1999 | Harms et al. |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| 5,902,303 A | 5/1999 | Eckhof et al. |
| 5,938,663 A | 8/1999 | Petreto |
| 5,954,725 A | 9/1999 | Sherman et al. |
| 5,961,517 A | 10/1999 | Biedermann et al. |
| 5,964,760 A | 10/1999 | Richelsoph |
| 6,010,503 A | 1/2000 | Richelsoph et al. |
| 6,019,759 A | 2/2000 | Rogozinski |
| 6,022,350 A | 2/2000 | Ganem |
| 6,053,917 A | 4/2000 | Sherman et al. |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,110,172 A | 8/2000 | Jackson |
| 6,113,601 A | 9/2000 | Tatar |
| 6,132,431 A | 10/2000 | Nilsson et al. |
| 6,132,432 A | 10/2000 | Richelsoph |
| 6,132,434 A | 10/2000 | Sherman et al. |
| 6,146,383 A | 11/2000 | Studer et al. |
| 6,183,472 B1 | 2/2001 | Lutz |
| 6,186,718 B1 | 2/2001 | Fogard |
| 6,187,005 B1 | 2/2001 | Brace et al. |
| 6,214,012 B1 | 4/2001 | Karpman et al. |
| RE37,161 E | 5/2001 | Michelson et al. |
| 6,224,596 B1 | 5/2001 | Jackson |
| 6,248,105 B1 | 6/2001 | Schlapfer et al. |
| 6,254,602 B1 | 7/2001 | Justis |
| 6,273,888 B1 | 8/2001 | Justis |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,296,642 B1 | 10/2001 | Morrison et al. |
| 6,302,888 B1 | 10/2001 | Mellinger et al. |
| 6,309,391 B1 | 10/2001 | Crandall et al. |
| 6,331,179 B1 | 12/2001 | Freid et al. |
| 6,355,040 B1 | 3/2002 | Richelsoph et al. |
| RE37,665 E | 4/2002 | Ralph et al. |
| 6,368,321 B1 | 4/2002 | Jackson |
| 6,371,957 B1 | 4/2002 | Amrein et al. |
| 6,402,752 B2 | 6/2002 | Schaffler-Wachter et al. |
| 6,440,137 B1 | 8/2002 | Horvath et al. |
| 6,451,021 B1 | 9/2002 | Ralph et al. |
| 6,471,703 B1 | 10/2002 | Ashman |
| 6,471,705 B1 | 10/2002 | Biedermann et al. |
| 6,485,494 B1 | 11/2002 | Haider |
| 6,488,681 B2 | 12/2002 | Martin et al. |
| 6,508,818 B2 | 1/2003 | Steiner et al. |
| 6,520,962 B1 | 2/2003 | Taylor et al. |
| 6,527,804 B1 | 3/2003 | Gauchet et al. |
| 6,530,929 B1 | 3/2003 | Justis et al. |
| 6,533,786 B1 | 3/2003 | Needham et al. |
| 6,547,790 B2 | 4/2003 | Harkey, III et al. |
| 6,551,320 B2 | 4/2003 | Lieberman |
| 6,554,832 B2 | 4/2003 | Shluzas |
| 6,554,834 B1 | 4/2003 | Crozet et al. |
| 6,558,387 B2 | 5/2003 | Errico et al. |
| 6,562,040 B1 | 5/2003 | Wagner |
| 6,565,565 B1 | 5/2003 | Yuan et al. |
| 6,565,567 B1 | 5/2003 | Haider |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Donno et al. |
| 6,610,063 B2 | 8/2003 | Kumar et al. |
| 6,613,050 B1 | 9/2003 | Wagner et al. |
| 6,623,485 B2 | 9/2003 | Doubler et al. |
| 6,626,907 B2 | 9/2003 | Campbell et al. |
| 6,626,908 B2 | 9/2003 | Cooper et al. |
| 6,635,059 B2 | 10/2003 | Randall et al. |
| 6,648,885 B1 | 11/2003 | Friesem |
| 6,648,887 B2 | 11/2003 | Ashman |
| 6,652,526 B1 | 11/2003 | Arafiles |
| 6,656,179 B1 | 12/2003 | Schaefer et al. |
| 6,656,181 B2 | 12/2003 | Dixon et al. |
| 6,660,004 B2 | 12/2003 | Barker et al. |
| 6,663,632 B1 | 12/2003 | Frigg |
| 6,663,635 B2 | 12/2003 | Frigg et al. |
| 6,673,073 B1 | 1/2004 | Schafer |
| 6,676,661 B1 | 1/2004 | Benlloch et al. |
| 6,679,833 B2 | 1/2004 | Smith et al. |
| 6,682,529 B2 | 1/2004 | Stahurski |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 | 5/2004 | Richelsoph |
| 6,746,449 B2 | 6/2004 | Jones et al. |
| 6,755,829 B1 | 6/2004 | Bono et al. |
| 6,755,835 B2 | 6/2004 | Schultheiss et al. |
| 6,755,836 B1 | 6/2004 | Lewis |
| 6,761,723 B2 | 7/2004 | Buttermann et al. |
| 6,767,351 B2 | 7/2004 | Orbay et al. |
| 6,770,075 B2 | 8/2004 | Howland |
| 6,780,186 B2 | 8/2004 | Errico et al. |
| 6,790,209 B2 | 9/2004 | Beale et al. |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,840,940 B2 | 1/2005 | Ralph et al. |
| 6,843,791 B2 | 1/2005 | Serhan |
| 6,858,031 B2 | 2/2005 | Morrison et al. |

| | | |
|---|---|---|
| 6,869,432 B2 | 3/2005 | Schlapfer et al. |
| 6,869,433 B2 | 3/2005 | Glascott |
| 6,872,208 B1 | 3/2005 | McBride et al. |
| 6,896,677 B1 | 5/2005 | Lin |
| 6,932,817 B2 | 8/2005 | Baynham et al. |
| 6,945,972 B2 | 9/2005 | Frigg et al. |
| 6,953,462 B2 | 10/2005 | Lieberman |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,974,460 B2 | 12/2005 | Carbone et al. |
| 6,979,334 B2 | 12/2005 | Dalton |
| 6,981,973 B2 | 1/2006 | McKinley |
| RE39,035 E | 3/2006 | Finn et al. |
| 7,018,378 B2 | 3/2006 | Biedermann et al. |
| 7,018,379 B2 | 3/2006 | Drewry et al. |
| 7,022,122 B2 | 4/2006 | Amrein et al. |
| RE39,089 E | 5/2006 | Ralph et al. |
| 7,066,062 B2 | 6/2006 | Flesher |
| 7,066,937 B2 | 6/2006 | Shluzas |
| 7,081,116 B1 | 7/2006 | Carly |
| 7,083,621 B2 | 8/2006 | Shaolian et al. |
| 7,087,057 B2 | 8/2006 | Konieczynski et al. |
| 7,090,674 B2 | 8/2006 | Doubler et al. |
| 7,121,755 B2 | 10/2006 | Schlapfer et al. |
| 7,125,426 B2 | 10/2006 | Moumene et al. |
| 7,128,743 B2 | 10/2006 | Metz-Stavenhagen |
| 7,141,051 B2 | 11/2006 | Janowski et al. |
| 7,144,396 B2 | 12/2006 | Shluzas |
| 7,163,538 B2 | 1/2007 | Altarac et al. |
| 7,163,539 B2 | 1/2007 | Abdelgany et al. |
| 7,166,108 B2 | 1/2007 | Mazda et al. |
| 7,186,255 B2 | 3/2007 | Baynham et al. |
| 7,211,086 B2 | 5/2007 | Biedermann et al. |
| 7,211,087 B2 | 5/2007 | Young |
| 7,214,227 B2 | 5/2007 | Colleran et al. |
| 7,223,268 B2 | 5/2007 | Biedermann |
| 7,264,621 B2 | 9/2007 | Coates et al. |
| 7,270,665 B2 | 9/2007 | Morrison et al. |
| 7,291,151 B2 | 11/2007 | Alvarez |
| 7,291,153 B2 | 11/2007 | Glascott |
| 7,294,127 B2 | 11/2007 | Leung et al. |
| 7,294,128 B2 | 11/2007 | Alleyne et al. |
| 7,294,129 B2 | 11/2007 | Hawkins et al. |
| 7,306,603 B2 | 12/2007 | Boehm, Jr. et al. |
| 7,306,604 B2 | 12/2007 | Carli |
| 7,306,606 B2 | 12/2007 | Sasing |
| 7,314,467 B2 | 1/2008 | Howland |
| 7,316,684 B1 | 1/2008 | Baccelli et al. |
| 7,322,979 B2 | 1/2008 | Crandall et al. |
| 7,335,201 B2 | 2/2008 | Doubler et al. |
| 7,335,202 B2 | 2/2008 | Matthis et al. |
| 7,338,490 B2 | 3/2008 | Ogilvie et al. |
| 7,338,491 B2 | 3/2008 | Baker et al. |
| 7,682,377 B2 * | 3/2010 | Konieczynski et al. ...... 606/269 |
| 2001/0001119 A1 | 5/2001 | Lombardo |
| 2002/0035366 A1 | 3/2002 | Walder et al. |
| 2002/0045898 A1 | 4/2002 | Freid et al. |
| 2002/0072751 A1 | 6/2002 | Jackson |
| 2002/0082602 A1 | 6/2002 | Biedermann et al. |
| 2002/0111626 A1 | 8/2002 | Ralph et al. |
| 2002/0133159 A1 | 9/2002 | Jackson |
| 2002/0143341 A1 | 10/2002 | Biedermann et al. |
| 2002/0173789 A1 | 11/2002 | Howland |
| 2002/0193795 A1 | 12/2002 | Gertzbein et al. |
| 2003/0023240 A1 | 1/2003 | Amrein et al. |
| 2003/0023243 A1 | 1/2003 | Biedermann et al. |
| 2003/0073996 A1 | 4/2003 | Doubler et al. |
| 2003/0093078 A1 | 5/2003 | Ritland |
| 2003/0100896 A1 | 5/2003 | Biedermann et al. |
| 2003/0105460 A1 | 6/2003 | Crandall et al. |
| 2003/0125741 A1 | 7/2003 | Biedermann et al. |
| 2003/0149432 A1 | 8/2003 | Frigg et al. |
| 2003/0153911 A1 | 8/2003 | Shluzas |
| 2003/0163133 A1 | 8/2003 | Altarac et al. |
| 2003/0176862 A1 | 9/2003 | Taylor et al. |
| 2003/0199873 A1 | 10/2003 | Richelsoph |
| 2003/0208204 A1 | 11/2003 | Bailey et al. |
| 2003/0216735 A1 | 11/2003 | Altarac et al. |
| 2004/0006342 A1 | 1/2004 | Altarac et al. |
| 2004/0092934 A1 | 5/2004 | Howland |
| 2004/0097933 A1 | 5/2004 | Lourdel et al. |
| 2004/0116929 A1 | 6/2004 | Barker et al. |
| 2004/0138662 A1 | 7/2004 | Landry et al. |
| 2004/0143265 A1 | 7/2004 | Landry et al. |
| 2004/0147929 A1 | 7/2004 | Biedermann et al. |
| 2004/0158247 A1 | 8/2004 | Sitiso et al. |
| 2004/0172022 A1 | 9/2004 | Landry et al. |
| 2004/0176766 A1 | 9/2004 | Shluzas |
| 2004/0186473 A1 | 9/2004 | Cournoyer et al. |
| 2004/0210216 A1 | 10/2004 | Farris et al. |
| 2004/0225289 A1 | 11/2004 | Biedermann et al. |
| 2004/0236330 A1 | 11/2004 | Purcell et al. |
| 2004/0249380 A1 | 12/2004 | Glascott |
| 2004/0267264 A1 | 12/2004 | Konieczynski et al. |
| 2005/0027296 A1 | 2/2005 | Thramann et al. |
| 2005/0055026 A1 | 3/2005 | Biedermann et al. |
| 2005/0070899 A1 | 3/2005 | Doubler et al. |
| 2005/0080415 A1 | 4/2005 | Keyer et al. |
| 2005/0096654 A1 | 5/2005 | Lin |
| 2005/0107788 A1 | 5/2005 | Beaurain et al. |
| 2005/0113927 A1 | 5/2005 | Malek |
| 2005/0131404 A1 | 6/2005 | Mazda et al. |
| 2005/0131413 A1 | 6/2005 | O'Driscoll et al. |
| 2005/0149023 A1 | 7/2005 | Ritland |
| 2005/0154389 A1 | 7/2005 | Selover et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0187548 A1 | 8/2005 | Butler et al. |
| 2005/0187555 A1 | 8/2005 | Biedermann et al. |
| 2005/0192580 A1 | 9/2005 | Dalton |
| 2005/0203511 A1 | 9/2005 | Wilson-MacDonald et al. |
| 2005/0203516 A1 | 9/2005 | Biedermann et al. |
| 2005/0216003 A1 | 9/2005 | Biedermann et al. |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0240181 A1 | 10/2005 | Boomer et al. |
| 2005/0240183 A1 | 10/2005 | Vaughan |
| 2005/0251137 A1 | 11/2005 | Ball |
| 2005/0251141 A1 | 11/2005 | Frigg et al. |
| 2005/0260058 A1 | 11/2005 | Cassagne, III |
| 2005/0261687 A1 | 11/2005 | Garamszegi et al. |
| 2005/0267474 A1 | 12/2005 | Dalton |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277925 A1 | 12/2005 | Mujwid |
| 2005/0277928 A1 | 12/2005 | Boschert |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0288669 A1 | 12/2005 | Abdou |
| 2005/0288671 A1 | 12/2005 | Yuan et al. |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009769 A1 | 1/2006 | Lieberman |
| 2006/0009770 A1 | 1/2006 | Speirs et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0036242 A1 | 2/2006 | Nilsson et al. |
| 2006/0036252 A1 | 2/2006 | Baynham et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0074419 A1 | 4/2006 | Taylor et al. |
| 2006/0079894 A1 | 4/2006 | Colleran et al. |
| 2006/0079895 A1 | 4/2006 | McLeer |

| | | | | | | |
|---|---|---|---|---|---|---|
| 2006/0079899 A1 | 4/2006 | Ritland | | 2007/0118118 A1 | 5/2007 | Kwak et al. |
| 2006/0084981 A1 | 4/2006 | Shluzas | | 2007/0118123 A1 | 5/2007 | Strausbaugh et al. |
| 2006/0084989 A1 | 4/2006 | Dickinson et al. | | 2007/0118124 A1 | 5/2007 | Biedermann et al. |
| 2006/0084993 A1 | 4/2006 | Landry et al. | | 2007/0123862 A1 | 5/2007 | Warnick |
| 2006/0084995 A1 | 4/2006 | Biedermann et al. | | 2007/0123864 A1 | 5/2007 | Walder et al. |
| 2006/0089643 A1 | 4/2006 | Mujwid | | 2007/0123867 A1 | 5/2007 | Kirschman |
| 2006/0089644 A1 | 4/2006 | Felix | | 2007/0123870 A1 | 5/2007 | Jeon et al. |
| 2006/0095037 A1 | 5/2006 | Jones et al. | | 2007/0161986 A1 | 7/2007 | Levy |
| 2006/0100622 A1 | 5/2006 | Jackson | | 2007/0161994 A1 | 7/2007 | Lowery et al. |
| 2006/0106380 A1 | 5/2006 | Colleran et al. | | 2007/0161995 A1 | 7/2007 | Trautwein et al. |
| 2006/0106383 A1 | 5/2006 | Biedermann et al. | | 2007/0161996 A1 | 7/2007 | Biedermann et al. |
| 2006/0116677 A1 | 6/2006 | Burd et al. | | 2007/0161999 A1 | 7/2007 | Biedermann et al. |
| 2006/0129147 A1 | 6/2006 | Biedermann et al. | | 2007/0167948 A1 | 7/2007 | Abdou |
| 2006/0129149 A1 | 6/2006 | Iott et al. | | 2007/0167949 A1 | 7/2007 | Altarac et al. |
| 2006/0142761 A1 | 6/2006 | Landry et al. | | 2007/0173819 A1 | 7/2007 | Sandlin |
| 2006/0149232 A1 | 7/2006 | Sasing | | 2007/0173820 A1 | 7/2007 | Trieu |
| 2006/0149241 A1 | 7/2006 | Richelsoph et al. | | 2007/0173828 A1 | 7/2007 | Firkins et al. |
| 2006/0149244 A1 | 7/2006 | Amrein et al. | | 2007/0191839 A1 | 8/2007 | Justis et al. |
| 2006/0155277 A1 | 7/2006 | Metz-Stavenhagen | | 2007/0198014 A1 | 8/2007 | Graf et al. |
| 2006/0155278 A1 | 7/2006 | Warnick | | 2007/0208344 A1 | 9/2007 | Young |
| 2006/0161152 A1 | 7/2006 | Ensign et al. | | 2007/0225707 A1 | 9/2007 | Wisnewski et al. |
| 2006/0167455 A1 | 7/2006 | Clement et al. | | 2007/0225711 A1 | 9/2007 | Ensign |
| 2006/0173454 A1 | 8/2006 | Spitler et al. | | 2007/0233078 A1 | 10/2007 | Justis et al. |
| 2006/0173456 A1 | 8/2006 | Hawkes et al. | | 2007/0233080 A1 | 10/2007 | Na et al. |
| 2006/0195198 A1 | 8/2006 | James | | 2007/0233086 A1 | 10/2007 | Harms et al. |
| 2006/0200123 A1 | 9/2006 | Ryan | | 2007/0233087 A1 | 10/2007 | Schlapfer |
| 2006/0200131 A1 | 9/2006 | Chao et al. | | 2007/0250061 A1 | 10/2007 | Chin et al. |
| 2006/0200149 A1 | 9/2006 | Hoy et al. | | 2007/0260243 A1 | 11/2007 | Kagami |
| 2006/0212034 A1 | 9/2006 | Triplett et al. | | 2007/0270806 A1 | 11/2007 | Foley et al. |
| 2006/0217716 A1 | 9/2006 | Baker et al. | | 2007/0270807 A1 | 11/2007 | Armstrong et al. |
| 2006/0229614 A1 | 10/2006 | Foley et al. | | 2007/0270810 A1 | 11/2007 | Sanders |
| 2006/0229615 A1 | 10/2006 | Abdou | | 2007/0270813 A1 | 11/2007 | Garamszegi |
| 2006/0235389 A1 | 10/2006 | Albert et al. | | 2007/0270815 A1 | 11/2007 | Johnson et al. |
| 2006/0235392 A1 | 10/2006 | Hammer et al. | | 2007/0270830 A1 | 11/2007 | Morrison |
| 2006/0235393 A1 | 10/2006 | Bono et al. | | 2007/0270831 A1 | 11/2007 | Dewey et al. |
| 2006/0241593 A1 | 10/2006 | Sherman et al. | | 2007/0270832 A1 | 11/2007 | Moore |
| 2006/0241595 A1 | 10/2006 | Molz et al. | | 2007/0270835 A1 | 11/2007 | Wisnewski |
| 2006/0241599 A1 | 10/2006 | Konieczynski et al. | | 2007/0270839 A1 | 11/2007 | Jeon et al. |
| 2006/0241600 A1 | 10/2006 | Ensign et al. | | 2007/0288004 A1 | 12/2007 | Alvarez |
| 2006/0247624 A1 | 11/2006 | Banouskou et al. | | 2008/0009862 A1 | 1/2008 | Hoffman |
| 2006/0247631 A1 | 11/2006 | Ahn et al. | | 2008/0009864 A1 | 1/2008 | Forton et al. |
| 2006/0247636 A1 | 11/2006 | Yuan et al. | | 2008/0015578 A1 | 1/2008 | Erickson et al. |
| 2006/0247779 A1 | 11/2006 | Gordon et al. | | 2008/0015579 A1 | 1/2008 | Whipple |
| 2006/0264933 A1 | 11/2006 | Baker et al. | | 2008/0015580 A1 | 1/2008 | Chao |
| 2006/0264936 A1 | 11/2006 | Partin et al. | | 2008/0015584 A1 | 1/2008 | Richelsoph |
| 2006/0276787 A1 | 12/2006 | Zubok et al. | | 2008/0015586 A1 | 1/2008 | Krishna et al. |
| 2006/0276791 A1 | 12/2006 | Shluzas | | 2008/0021454 A1 | 1/2008 | Chao et al. |
| 2006/0276792 A1 | 12/2006 | Ensign et al. | | 2008/0021455 A1 | 1/2008 | Chao et al. |
| 2006/0282074 A1 | 12/2006 | Renaud et al. | | 2008/0021462 A1 | 1/2008 | Trieu |
| 2006/0293659 A1 | 12/2006 | Alvarez | | 2008/0021464 A1 | 1/2008 | Morin et al. |
| 2006/0293665 A1 | 12/2006 | Shluzas | | 2008/0021473 A1 | 1/2008 | Butler et al. |
| 2006/0293666 A1 | 12/2006 | Matthis et al. | | 2008/0027432 A1 | 1/2008 | Strauss et al. |
| 2007/0016188 A1 | 1/2007 | Boehm, Jr. et al. | | 2008/0039838 A1 | 2/2008 | Landry et al. |
| 2007/0016198 A1 | 1/2007 | Boehm, Jr. et al. | | 2008/0039843 A1 | 2/2008 | Abdou |
| 2007/0021750 A1 | 1/2007 | Shluzas et al. | | 2008/0045951 A1 | 2/2008 | Fanger et al. |
| 2007/0043355 A1 | 2/2007 | Bette et al. | | 2008/0045955 A1 | 2/2008 | Berrevoets et al. |
| 2007/0043357 A1 | 2/2007 | Kirschman | | 2008/0045957 A1 | 2/2008 | Landry et al. |
| 2007/0043358 A1 | 2/2007 | Molz, IV et al. | | 2008/0051780 A1 | 2/2008 | Vaidya et al. |
| 2007/0043359 A1 | 2/2007 | Altarac et al. | | 2008/0058811 A1 | 3/2008 | Alleyne et al. |
| 2007/0043364 A1 | 2/2007 | Cawley et al. | | 2008/0058812 A1 | 3/2008 | Zehnder |
| 2007/0049933 A1 | 3/2007 | Ahn et al. | | 2008/0065073 A1 | 3/2008 | Perriello et al. |
| 2007/0055235 A1 | 3/2007 | Janowski et al. | | 2008/0065077 A1 | 3/2008 | Ferree |
| 2007/0055238 A1 | 3/2007 | Biedermann et al. | | 2008/0071273 A1 | 3/2008 | Hawkes et al. |
| 2007/0055239 A1 | 3/2007 | Sweeney et al. | | 2008/0071274 A1 | 3/2008 | Ensign |
| 2007/0055240 A1 | 3/2007 | Matthis et al. | | 2008/0071277 A1 | 3/2008 | Warnick |
| 2007/0055241 A1 | 3/2007 | Matthis et al. | | 2008/0132957 A1* | 6/2008 | Matthis et al. ............... 606/301 |
| 2007/0055242 A1 | 3/2007 | Bailly | | | | |
| 2007/0073291 A1 | 3/2007 | Cordaro et al. | | FOREIGN PATENT DOCUMENTS | | |
| 2007/0078460 A1 | 4/2007 | Frigg et al. | | | | |
| 2007/0083199 A1 | 4/2007 | Baccelli | | EP | 1190678 | 3/2002 |
| 2007/0088357 A1 | 4/2007 | Johnson et al. | | EP | 1570795 | 9/2005 |
| 2007/0093817 A1 | 4/2007 | Barrus et al. | | EP | 1634537 | 3/2006 |
| 2007/0093818 A1 | 4/2007 | Biedermann et al. | | GB | 2365345 | 2/2002 |
| 2007/0093819 A1 | 4/2007 | Albert | | WO | WO 01/49191 | 7/2001 |
| 2007/0093826 A1 | 4/2007 | Hawkes et al. | | WO | WO02/054966 | 7/2002 |
| 2007/0093827 A1 | 4/2007 | Warnick | | WO | WO03/068088 | 8/2003 |
| 2007/0093831 A1 | 4/2007 | Abdelgany et al. | | WO | WO2004/041100 | 5/2004 |
| 2007/0100341 A1 | 5/2007 | Reglos et al. | | WO | WO2004/089245 | 10/2004 |
| 2007/0118117 A1 | 5/2007 | Altarac et al. | | WO | WO2004/107997 | 12/2004 |
| | | | | WO | WO2005/000136 | 1/2005 |

| WO | WO2005/000137 | 1/2005 |
| WO | WO2005/020829 | 3/2005 |
| WO | WO2005/072632 | 8/2005 |
| WO | WO2005/082262 | 9/2005 |
| WO | WO 2005/099400 | 10/2005 |
| WO | WO 2006/005198 | 1/2006 |
| WO | WO 2006/012088 | 2/2006 |
| WO | WO 2006/017616 | 2/2006 |
| WO | WO 2006/028537 | 3/2006 |
| WO | WO 2006/119241 | 11/2006 |
| WO | WO 2007/118045 | 10/2007 |
| WO | WO2007/124222 | 11/2007 |
| WO | WO 2007/0130835 | 11/2007 |
| WO | WO 2007/130840 | 11/2007 |
| WO | WO 2007/130941 | 11/2007 |

OTHER PUBLICATIONS

*Claris Instrumentation* Brochure, G Med, pub. 1997.
*VLS System Variable Locking Screw* Brochure, Interpore Cross International, 1999.
*CD Horizon M8 Multi Axial Screw Spinal System* Brochure, Medtronic Sofamor Danek, no publish date.
*Contour Spinal System* Brochure, Ortho Development, no publish date.
*Xia Spinal System* Brochure, Stryker Howmedica Osteonics, no publish date.
*The Rod Plate System* Brochure, Stryker Howmedica Osteonics, pub. Oct. 1999.
*Silhouette Spinal Fixation System* Brochure, Sulzer Medica Spine-Tech, no publish date.
*SDRS Surgical Dynamics Rod System* Brochure, Surgical Dynamics, pub. 1998-1999.
*Versalok Low Back Fixation System* Brochure, Wright Medical Technology, Inc., pub. 1997.
*The Strength of Innovation* Advertisement, Blackstone Medical Inc., no publish date.
*The Moss Miami 6.0mm System* Advertisement, author unknown, no publish date.

\* cited by examiner

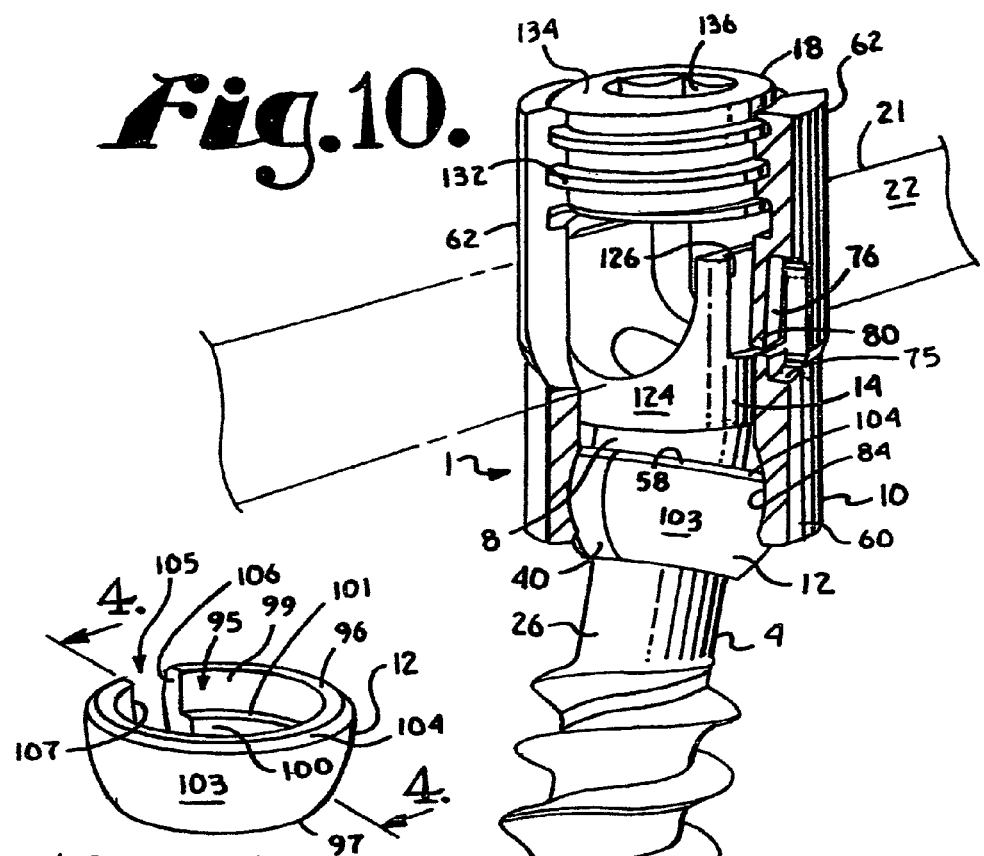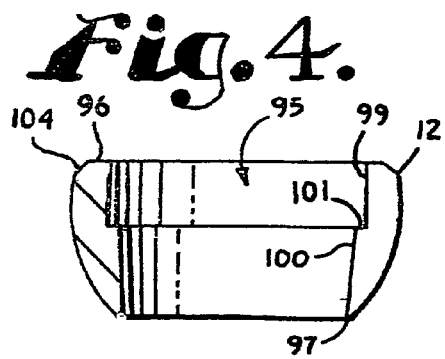

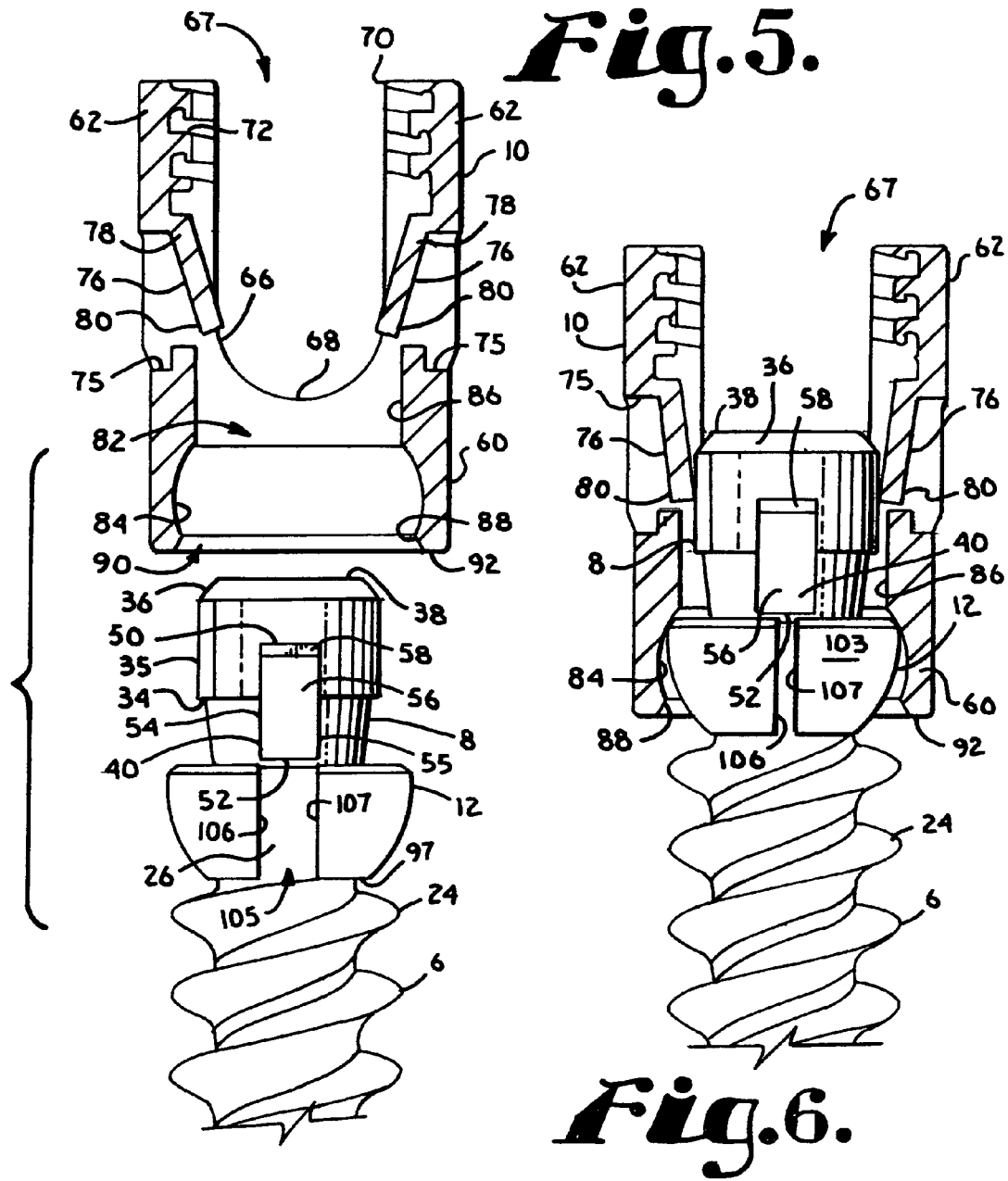

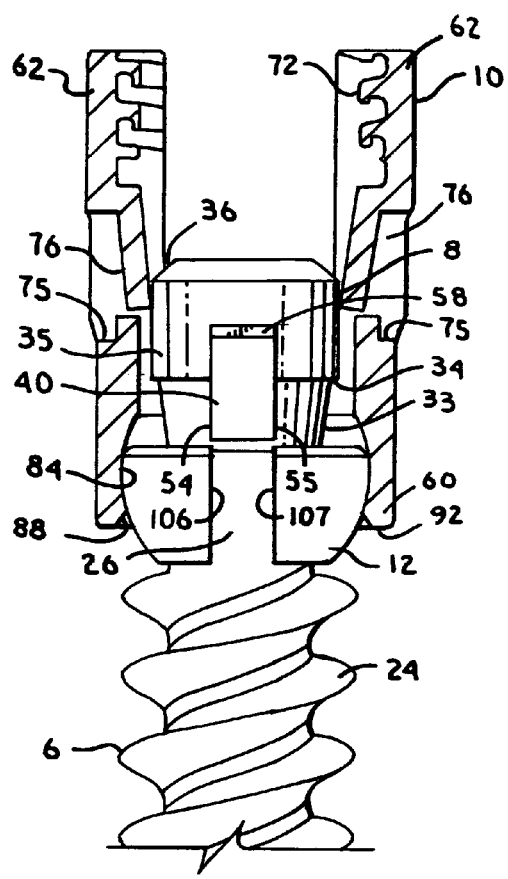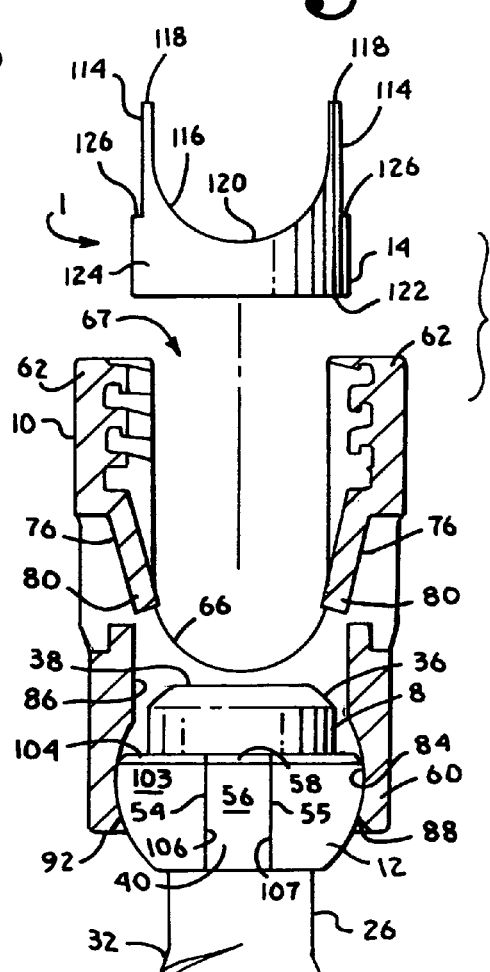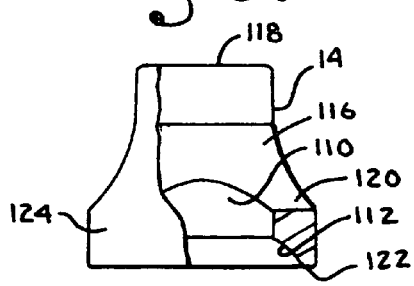

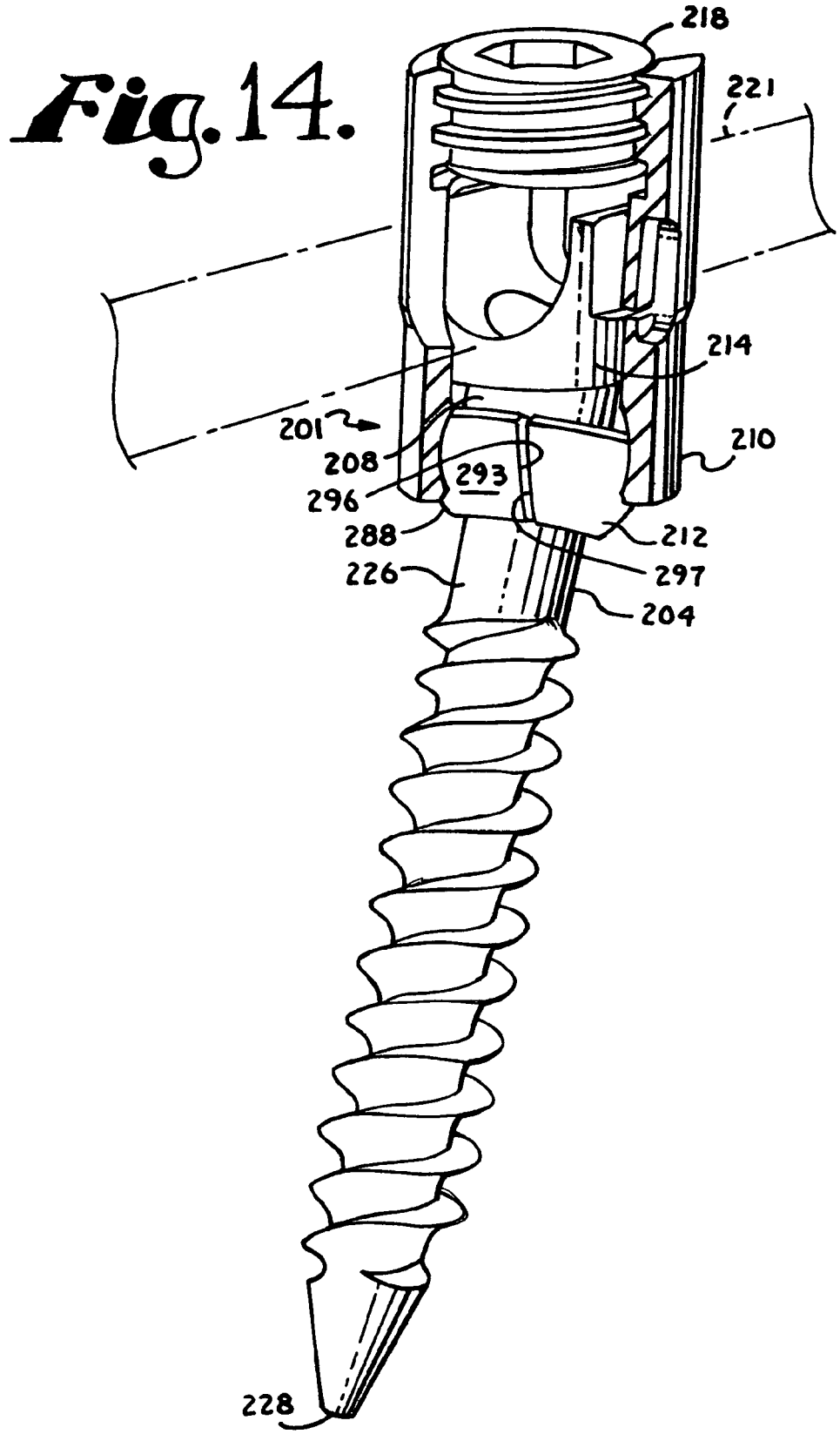

POLYAXIAL BONE SCREW WITH SHANK-RETAINER INSET CAPTURE

CROSS-REFERENCE TO RELATED APPLICATIONS

This application claims the benefit of U.S. Provisional Application No. 60/931,362 filed May 23, 2007, and incorporated by reference herein. This application is also a continuation-in-part of U.S. patent application Ser. No. 10/818,555 filed Apr. 5, 2004, now U.S. Pat. No. 8,052,724 that is a continuation of U.S. patent application Ser. No. 10/464,633 filed Jun. 18, 2003, now U.S. Pat. No. 6,716,214 and a continuation-in-part of U.S. patent application Ser. No. 10/651,003, filed Aug. 28, 2003, now U.S. Pat. No. 8,137,386, all of which are incorporated by reference herein. This application is also a continuation-in-part of U.S. patent application Ser. No. 11/140,343 filed May 27, 2005, also incorporated by reference herein.

BACKGROUND OF THE INVENTION

The present invention is directed to polyaxial bone screws for use in bone surgery, particularly spinal surgery, and particularly to capture structures and inserts for such screws.

Bone screws are utilized in many types of spinal surgery in order to secure various implants to vertebrae along the spinal column for the purpose of stabilizing and/or adjusting spinal alignment. Although both closed-ended and open-ended bone screws are known, open-ended screws are particularly well suited for connections to rods and connector arms, because such rods or arms do not need to be passed through a closed bore, but rather can be laid or urged into an open channel within a receiver or head of such a screw.

Typical open-ended bone screws include a threaded shank with a pair of parallel projecting branches or arms which form a yoke with a U-shaped slot or channel to receive a rod. Hooks and other types of connectors, as are used in spinal fixation techniques, may also include open ends for receiving rods or portions of other structure.

A common mechanism for providing vertebral support is to implant bone screws into certain bones which then in turn support a longitudinal structure such as a rod, or are supported by such a rod. Bone screws of this type may have a fixed head or receiver relative to a shank thereof. In the fixed bone screws, the rod receiver head cannot be moved relative to the shank and the rod must be favorably positioned in order for it to be placed within the receiver head. This is sometimes very difficult or impossible to do. Therefore, polyaxial bone screws are commonly preferred.

Open-ended polyaxial bone screws allow rotation of the head or receiver about the shank until a desired rotational position of the head is achieved relative to the shank. Thereafter, a rod can be inserted into the head or receiver and eventually the receiver is locked or fixed in a particular position relative to the shank.

During the rod implantation process it is desirable to utilize bone screws or other bone anchors that have components that remain within the bone screw and further remain properly aligned during what is sometimes a very lengthy, difficult procedure. For example, some bone screws desirably include compression inserts or other parts that are designed to securely and fully engage surface portions of a rod or other longitudinal connecting member.

SUMMARY OF THE INVENTION

A polyaxial bone screw assembly of the present invention includes a shank having a generally elongate body with an upper end portion a neck below the upper end portion and a lower threaded portion for fixation to a bone. The upper end portion includes at least first and second surfaces, the second surface being at least partially inset or at least a portion thereof spaced inwardly from the first surface. For example, the first and second surfaces may be in the form of two substantially cylindrical surface portions of different widths or diameters or a cylindrical surface portion and a conical surface portion that is inset from the cylindrical surface portion. Alternatively, the upper end portion may include a laterally extending alignment structure in the form of a fin, rib or lug that can at least partially fill a gap or slot in a retainer component and block rotation between these two parts.

The bone screw assembly further includes a lockable receiver coupling member having a top portion and a base. The top portion is open and has a channel. The base includes an inner surface partially defining a cavity and a lower aperture or opening to an exterior of the base. The channel of the top portion communicates with the cavity, which in turn communicates with the base lower opening; such opening is sized and shaped to receive the shank upper end portion into the receiver cavity. The parts are arranged such that the shank neck is in close alignment with and positioned directly below the receiver cavity.

The bone screw assembly also includes an open ring-like retainer structure defining a gap or slit and further having a discontinuous internal surface sized and shaped to be received over the lower conical or cylindrical surface portion to capture, house and hold the retainer and shank upper end portion within the lockable receiver coupling member. In the illustrated embodiment, the fin of the shank upper portion is disposed within the gap or slit of the retainer structure. The external surface of the retainer structure is configured to be in slidable, pivotable engagement with a seating surface defining a portion of the cavity of the receiver. Preferably, the retainer structure external surface and the mating receiver inner seating surface are substantially spherical. However, it is noted that the mating surfaces may be of another shape, such as conical, cylindrical or tapered, especially for the receiver cavity inner seating surface. The cooperating shapes of the retainer external surface and the receiver seating surface enable selective angular positioning of the shank body with respect to the receiver.

The illustrated bone screw assembly further includes a compression or pressure insert disposed between the shank upper portion and a longitudinal connecting member, such as a rod, being held in place by the bone screw. An upper or top surface of the shank upper end portion is sized and shaped for frictionally engagement with a lower surface of the pressure insert. In one embodiment according to the invention, the shank upper portion includes a tool engagement formation with an internal drive. The shank upper top surface can include knurling and the shank upper portion is sized in axial length such that the shank upper surface engages the compression insert at a location substantially spaced from the retainer structure. Thus, at any operational pivoted position of the bone screw shank with respect to the receiver, the compression insert is always spaced from the retainer structure and never engages the same, advantageously providing for the exertion of pressure exclusively onto the stronger integral shank upper portion. The retainer structure of the present invention is split and thus could become twisted or misaligned if placed under the opposing shear forces and even torsional forces caused if the pressure insert were allowed to press upon an edge or surface of the retainer structure when it is in a pivoted, angled or oblique position. In the embodiments of the present invention, the shank upper end portion includes an axially directed length adequate to prevent such undesirable engagement between the pressure insert and the retainer structure. The retainer structure is advantageously disposed substantially below the pressure insert and between the shank upper portion and the receiver seating surface, with only the shank upper portion pressing the retainer structure against the receiver seating surface. The fact that the retainer structure can only engage the shank upper end portion and the receiver, and never the pressure insert, and still move in a polyaxial way with respect to the receiver is a unique and novel feature for the invention.

OBJECTS AND ADVANTAGES OF THE INVENTION

Therefore, objects of the invention include: providing a polyaxial bone screw having a shank with off-set surfaces that cooperate with a retaining structure that is configured with inset capture surfaces for retaining an upper portion of the shank in a lockable bone screw receiver coupling member and also configured for polyaxial motion with respect to the receiver prior to locking; providing such a polyaxial bone screw that includes a pressure insert that exerts pressure exclusively on the integral and stronger shank upper end portion and that is substantially spaced from the retaining structure; providing a lightweight, low profile polyaxial bone screw that assembles in such a manner that the components cooperate to create an overall structure that prevents unintentional disassembly; providing a polyaxial bone screw with features that provide adequate frictional or gripping surfaces for bone implantation tools and may be readily, securely fastened to each other and to bone; and providing apparatus and methods that are easy to use and especially adapted for the intended use thereof and wherein the apparatus are comparatively inexpensive to make and suitable for use.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 3 is an enlarged perspective view of the retainer of FIG. 1.

FIG. 4 is an enlarged cross-sectional view taken along the line 4-4 of FIG. 3.

FIG. 5 is an enlarged and partial exploded front elevational view of the shank, retainer and receiver of FIG. 1 with portions broken away to show the detail thereof showing the shank and retainer in a first stage of assembly.

FIG. 6 is an enlarged and partial front elevational view similar to FIG. 5 showing the shank being uploaded into the retainer in a subsequent stage of assembly.

FIG. 7 is an enlarged and partial front elevational view similar to FIG. 6 showing a subsequent stage of assembly.

FIG. 8 is an enlarged and partial front elevational view similar to FIG. 7 and also including the compression insert, showing a subsequent stage of assembly.

FIG. 9 is an enlarged side elevational view of the compression insert of FIG. 1 with portions broken away to show the detail thereof.

FIG. 10 is an enlarged perspective view of the assembly of FIG. 1 shown assembled with a rod and with portions broken away to show the detail thereof.

FIG. 14 is an enlarged perspective view of the assembly of FIG. 11 shown assembled with a rod and with portions broken away to show the detail thereof.

DETAILED DESCRIPTION OF THE INVENTION

Figure 1:
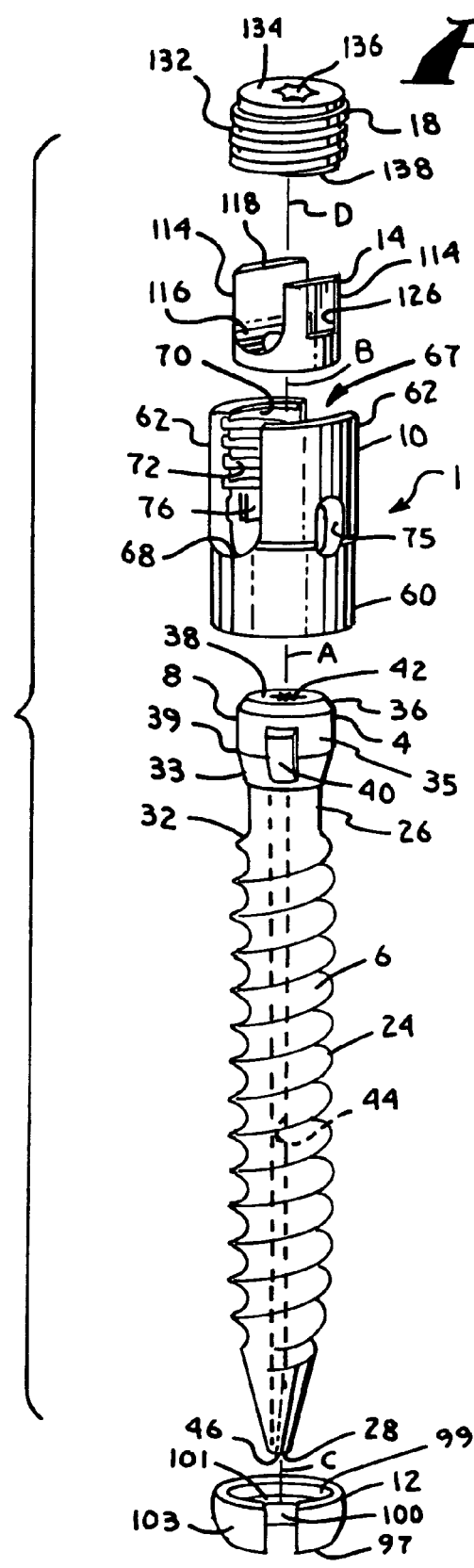
FIG. 1 is an exploded perspective view of a polyaxial bone screw assembly according to the present invention having a shank, a receiver, a retainer and a compression insert and further shown with a closure structure.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of bone attachment assemblies of the application and cooperating connecting members in actual use.

With reference to FIGS. 1-10, the reference number 1 generally represents an embodiment of a polyaxial bone screw apparatus or assembly according to the present invention. The assembly 1 includes a shank 4 that further includes a threaded body 6 integral with an upper portion 8; a receiver 10; an open retainer structure or ring 12; and a compression insert 14. The shank 4, receiver 10, retainer structure 12, and compression insert 14 preferably are factory assembled prior to implantation of the shank body 6 into a vertebra (not shown).

With further reference to FIG. 1, also shown is a closure structure 18 for biasing a longitudinal connecting member such as a rod 21 having a cylindrical surface 22 against the compression insert 14 that in turn presses upon the shank upper portion 8 which biases the retainer 12 into fixed frictional contact with the receiver 10, so as to fix the rod 21 relative to the vertebra (not shown). The receiver 10 and the shank 4 cooperate in such a manner that the receiver 10 and the shank 4 can be secured at any of a plurality of angles, articulations or pivotal alignments relative to one another and within a selected range of angles both from side to side and from front to rear, to enable flexible or articulated engagement of the receiver 10 with the shank 4 until both are locked or fixed relative to each other near the end of an implantation procedure.

Figure 2:
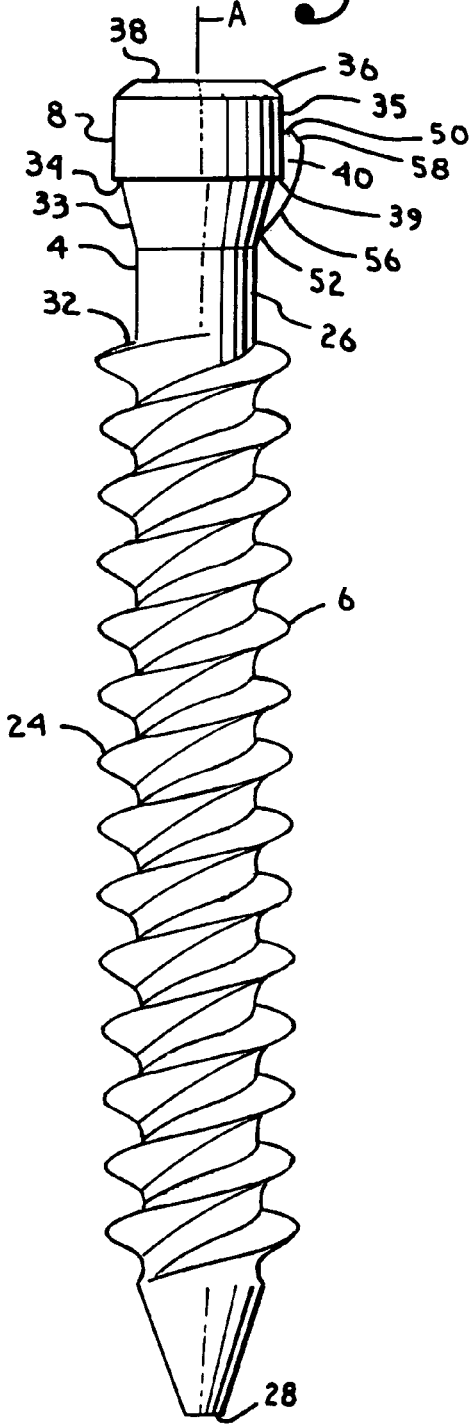
FIG. 2 is an enlarged front elevational view of the shank of FIG. 1.

The shank 4, best illustrated in FIGS. 1, 2 and 5, is elongate, with the shank body 6 having a helically wound bone implantable thread 24 extending from near a neck 26 located adjacent to the upper portion 8 to a tip 28 of the body 6 and extending radially outwardly therefrom. During use, the body 6 utilizing the thread 24 for gripping and advancement is implanted into the vertebra (not shown) leading with the tip 28 and driven down into the vertebra with an installation or driving tool, so as to be implanted in the vertebra to near the neck 26, and as is described more fully in the paragraphs below. The shank 4 has an elongate axis of rotation generally identified by the reference letter A.

The neck 26 extends axially upwardly from the shank body 6. The neck 26 may be of reduced radius as compared to an adjacent top 32 of the threaded body 6. Further extending axially upwardly from the neck 26 is the shank upper portion 8 that provides a connective or capture apparatus disposed at a distance from the threaded body top 32 and thus at a distance from the vertebra when the body 6 is implanted in the vertebra.

The shank upper portion 8 is configured for a polyaxial connection between the shank 4 and the receiver 10 and capturing the shank 4 upper portion 8 in the receiver 10. The illustrated upper portion 8 generally includes an outer conical surface portion 33 located adjacent the neck 26; an annular planar retainer seat portion 34; a substantially cylindrical surface portion 35; a curved and annular upper surface 36 and a planar top surface 38. The planar top surface 38 is substantially perpendicular to the cylindrical surface portion 35 and substantially parallel to the seat portion 34. As shown in the drawings and described more fully below, the height of the portion 35 along the axis A ensures that the cooperating lower pressure insert 14 is separated from and never engages the retainer 12 throughout a full range of polyaxial motion of the assembly 1 in all directions. The conical portion 33 extends between the neck 26 and the retainer seat 34. The retainer seat 34 defines a lower edge 39 of the cylindrical portion 35. A structure in the form of a rib or fin 40 extends laterally from the conical portion 33 and a lower part of the cylindrical portion 35. A tool engagement internal drive feature or structure 42 is formed in the top end surface 38. A driving tool (not shown) has a driving projection configured to fit within the tool engagement structure 42 for both driving and rotating the shank body 6 into the vertebra.

The upper surface 36 of the shank 4 is preferably curved or radiused as shown in the drawings, for contact engagement or positive mating engagement with the compression insert 14, when the bone screw assembly 1 is assembled, as shown in FIG. 10 and in any pivotal alignment of the shank 4 relative to the receiver 10. The illustrated surface 36 also has approximately the same radius as an inner spherical seating surface of the receiver 10, allowing for clearance of the shank 4 with respect to the receiver 10 and thus a desired degree and magnitude of articulation of the shank 4 with respect to the receiver 10, as will be described in greater detail below. In certain embodiments, the surface 36 is smooth. While not required in accordance with the practice of the invention, the surface 36 may be scored or knurled to further increase frictional positive mating engagement between the surface 36 and the compression insert 14.

The shank 4 shown in the drawings is cannulated, having a small central bore 44 extending an entire length of the shank 4 along the axis A. The bore 44 is defined by an inner cylindrical wall of the shank 4 and has a circular opening 46 at the shank tip 28 and an upper opening communicating with the internal drive 42. The bore 44 is coaxial with the threaded body 6 and the upper portion 8. The bore 44 provides a passage through the shank 4 interior for a length of wire (not shown) inserted into the vertebra (not shown) prior to the insertion of the shank body 6, the wire providing a guide for insertion of the shank body 6 into the vertebra (not shown).

With reference to FIGS. 2 and 5, the retainer seat 34 of the shank upper portion 8 is formed by the off-set positioning and cooperation of the surface portions 33 and 35. The off-set nature of the surface portion 35 with respect to the surface portion 33 creates the surface 34 that is substantially planar, annular and disposed perpendicular to the axis A of the shank and sized and shaped to engage the retainer structure 12, as will be described in greater detail below. The illustrated conical surface portion 33 is primarily sized and shaped for full frictional engagement with the retainer structure 12. The illustrated cylindrical surface portion 35 is sized and shaped to have a portion thereof being in frictional engagement with a portion of the retainer structure 12. Furthermore, the surface portion 34 is sized and shaped to provide a space between the structure 12 and the compression insert 14. Specifically, the cylindrical surface portion 35 has an axial length (with respect to the axis A) that is sufficient to keep an engaged retainer structure 12 in spaced apart relation with an engaged insert 14 in any and all angles, articulations or pivotal alignments of the shank 4 with respect to the receiver 10. Thus, at no time during assembly or operation does the insert 14 directly engage the retainer structure 12 (see FIG. 10, for example).

The rib or fin 40 that extends radially outwardly from both the conical portion 33 and a part of the cylindrical portion 35 includes a top surface 50, a bottom surface 52, a pair of opposed and substantially parallel side surfaces 54 and 55, an outer curved surface 56 and a bevel 58 disposed between the top surface 50 and the outer curved surface 56. In the illustrated embodiment, the bottom surface 52 is a narrow rim extending between the outer curved surface 56 and the conical surface portion 33 of the shank upper portion 8 that is disposed near the neck 26. The top surface 50 is substantially planar, disposed substantially perpendicular to the axis A and extending from the cylindrical surface portion 35 at a location spaced from the curved upper surface 36. The surfaces 56 and 58 are flush with outer surfaces of the retainer structure 12 when the seat 34 operatively engages the retainer 12 as will be discussed in greater detail below.

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetracalcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding. In association with such coating of the shank, the lockable receiver coupling member can be configured to rigidly lock onto a bored element or sleeve member that can slide on the rod or core longitudinal connecting member even after rigid locking together of the receiver and the shank, thereby allowing continued motion of the spine.

Referring to FIGS. 1 and 5, the receiver 10 has a generally U-shaped appearance with a partially cylindrical inner profile and a substantially curved or cylindrical outer profile; however, the outer profile could also be of another configuration, for example, faceted. The receiver has an axis of rotation B that is shown in FIG. 1 as being aligned with and the same as the axis of rotation A of the shank 4, such orientation being desirable during assembly of the receiver 10 with the shank 4, the retainer structure 12 and the insert 14. With reference to FIG. 10, after the receiver 10 is pivotally attached to the shank 4, and the assembly 1 is implanted in a vertebra (not shown), the axis B is typically disposed at an angle with respect to the axis A of the shank 4.

The receiver 10 includes a base 60 integral with a pair of opposed substantially similar or identical upstanding arms 62 forming a U-shaped cradle and defining a U-shaped channel 66 between the arms 62 with an upper opening 67 and a lower seat 68 having substantially the same radius as the rod 21 for operably receiving the rod 21. Each of the arms 62 has an interior surface 70 that defines the inner cylindrical profile and includes a partial helically wound guide and advancement structure 72. In the illustrated embodiment, the guide and advancement structure 72 is a partial helically wound interlocking flange form configured to mate under rotation with a similar structure on the closure structure 18, as described more fully below. However, it is foreseen that the guide and advancement structure 72 could alternatively be a square thread, a buttress thread, a reverse angle thread or other thread like or non-thread like helically wound advancement structure for operably guiding under rotation and advancing the closure top downward between the arms 62.

Tool engaging apertures 75 are formed on or through surfaces of the arms 62 that may be used for holding the receiver 10 during assembly with the shank 4 and the retainer structure 12 and also during the implantation of the shank body 6 into a vertebra (not shown). It is foreseen that tool receiving grooves or apertures may be configured in a variety of shapes and sizes and be disposed at other locations on the receiver arms 62.

A pair of spring tabs 76, each having an upper body portion 78 integral with a respective arm 62, and a lower end 80 extending downwardly and inwardly from the respective upper body portion 78. The tabs 76 are generally directed towards the axis B and downwardly away from the guide and advancement structure 72. The lower ends 80 are thus positioned to engage the compression insert 14 and hold such insert in a desired position as will be described in greater detail below. The tabs 76 are typically initially disposed parallel to the axis B and then a tool (not shown) is inserted into the aperture 75 from outside of the receiver 10 to engage and push the respective tab 76, thereby bending the tab 76 inwardly in a direction toward the axis B until the tab 76 is at a desired angular position, such as is illustrated in FIG. 5. Such bending of the tabs 76 may be performed either prior to or after assembly of the receiver 10 with the insert 14, the shank 4 and the retainer 12. In the illustrated embodiment, the tabs 76 are bent inwardly prior to installation with the components 14, 4 and 12. It is also foreseen that the tabs 76 may be machined or otherwise pre-fabricated to be angled or directed toward the axis B so as to engage the insert 14 as shown in the drawing figures. The illustrated tabs 76 are resilient, having a spring-like nature. Thus, when operatively cooperating with the insert 14, the tabs 76 bias against the insert 14, holding such insert in a desired position; and yet the tabs 76 are flexible enough to allow a user to make desired adjustments of the position of the insert 14 within the receiver 10. The tabs could be replaced with crimp holes.

With further reference to FIG. 5, communicating with and located beneath the U-shaped channel 66 of the receiver 10 is a chamber or cavity, generally 82, defined in part by an internal curvate or spherical seating surface 84 and an inner substantially cylindrical surface 86. The cylindrical surface 86 that defines a portion of the cavity 82 opens upwardly into the U-shaped channel 66. The inner surface 84 that is located below the surface 86 is sized and shaped for mating with the retainer structure 12, as described more fully below.

The base 60 further includes a restrictive neck 88 defining a bore, generally 90, communicating with the spherical surface 84 of the cavity 82 and also communicating with a lower exterior 92 of the base 60. The bore 90 is coaxially aligned with respect to the rotational axis B of the receiver 10. The neck 88 and associated bore 90 are sized and shaped to be smaller than an outer radial dimension of the retainer structure 12 when the structure 12 is attached to the shank upper portion 8, so as to form a restriction at the location of the neck 88 relative to the retainer structure 12, to prevent the retainer structure 12 and attached shank upper portion 8 from passing through the cavity 82 and out into the lower exterior 92 of the receiver 10.

The retainer structure or open ring 12 is used to capture the shank upper portion 8 and retain the upper portion 8 within the receiver 10 while being articulatable or pivotal in unison with the upper portion 8 within the receiver 10. The retainer 12, best illustrated in FIGS. 1 and 3-5, has an operational central axis that is the same as the rotational axis A associated with the shank 4, but when the retainer structure 12 is separated from the shank 4, the axis of rotation is identified as axis C, as shown in FIG. 1. The retainer structure 12 has a central bore, generally 95, that passes entirely through the retainer structure 12 from a top surface 96 to a bottom surface 97 thereof. Both the top surface 96 and the bottom surface 97 are substantially planar and disposed perpendicular to the axis C. An inner discontinuous and substantially cylindrical surface 99 defines a substantial portion of the bore 95. The cylindrical surface 99 is sized and shaped to be slidingly received and frictionally engaged about a lower section of the cylindrical surface portion 35 of the shank upper portion 8. The cylindrical surface 99 has an axial length (along the axis C) that is relatively small compared to an overall axial length of the retainer structure 12. Such relatively small axial length advantageously cooperates with the axial length of the cylindrical surface portion 35 of the shank upper portion 8 to provide sufficient space between the retainer structure 12 and the insert 14 during operation of the assembly 1. In the illustrated embodiment, an inner discontinuous substantially conical surface 100 defines a substantial portion of the bore 95. The conical surface 100 is sized and shaped to be slidingly received and frictionally engaged about the conical surface portion 33 of the shank upper portion 8. A discontinuous and substantially planar annular seating surface 101 is disposed between and connects the surface 99 with the off-set surface 100. The seating surface 101 is disposed substantially perpendicular to the axis C. The seating-surface 101 is sized and shaped to abut against and frictionally engage the seating surface 34 of the shank upper portion 8. The cooperating surfaces 99 and 35; 100 and 33; and 101 and 34 prohibit the retainer structure 12 from sliding off of the upper portion 8 in a direction toward the U-shaped channel 66. The retainer structure 12 further includes a discontinuous curvate or spherical outer surface 103 and a discontinuous bevel 104 disposed between the outer surface 103 and the top surface 96. A gap, generally 105 is defined by and disposed between facing side surfaces 106 and 107. The gap 105 or space between the surfaces 106 and 107 in this embodiment is sized for slidingly receiving the rib 40 between the surfaces 106 and 107. Surfaces 106 and 107 can be parallel or somewhat tapered and the fin can have matching side surfaces.

As will be described in greater detail below, the retainer structure 12 is somewhat flexible and resilient and may be manipulated or squeezed by moving the surfaces 106 and 107 toward one another as illustrated in FIG. 6 or, if necessary, slightly pulled apart for receiving the fin or rib 40 during assembly with the shank 4 as illustrated in FIGS. 7 and 8. The resilient nature of the structure 12 allows for the structure 12 to spring into an original shape as shown in FIGS. 1, 3 and 7 upon release of a manipulative compressing or pulling force.

The retainer structure 12 outer surface 103 can also be knurled and is sized and shaped to mate with the seating surface 84 of the receiver 10 which in addition can be knurled. When in a non-compressed state, a width of the surface 103 is larger than the width of the neck 88 of the receiver 10. The shank upper portion 8 conical surface 33, annular seat 34 and cylindrical surface 35, when engaged with the retainer 12, fix the retainer 12 at a desired diameter or width such that the retainer 12 is prohibited from moving through the receiver neck 88 and out of the receiver 10. Although not required, it is foreseen that the outer surface 103 may be a high friction surface such as a knurled surface, sand blasted surface, or the like. It is foreseen that in some embodiments of the invention, the retainer top surface 96 and the shank upper portion 8 may be configured so that the upper flat surface 96 abuts and supports a mating surface on the shank upper portion.

With reference to FIGS. 1 and 8-10, the compression insert 14 is sized and shaped to be received by and downloaded or uploaded into the receiver 10. In the illustrated embodiment, the insert 14 is downloaded into the receiver as shown in FIG. 8. In operation, the insert 14 is disposed between the rod 21 and the upper portion 8 of the bone screw 4 as illustrated, for example, in FIG. 10. When the closure structure 18 presses upon the rod 21, the rod 21 operatively presses upon the insert 14 that in turn presses exclusively upon the shank upper end portion 8, a portion of which is attached to the retainer 12, that, in turn, presses against the seating surface 84 of the receiver 10, resulting in ultimate frictional engagement and locking of the angular position of the bone screw shank 4 with respect to the receiver 10. The compression insert 14 has an operational central axis D that is the same as the central axis B of the receiver 10.

With particular reference to FIGS. 8-10, the compression insert 14 has a central channel or through bore substantially defined by a an inner cylindrical surface 110 and an inner partially spherical surface 112, both having the central axis D. The compression insert 14 through bore is sized and shaped to receive a driving tool (not shown) therethrough that engages the shank drive feature 42 when the shank body 6 is driven into bone. The surface 112 is sized and shaped to cooperate with the spherical or otherwise curvate surface 36 of the shank upper portion 8 for polyaxial motion of the screw 1 such that the surface 112 slidingly and pivotally mates with the surface 36. The surface 112 may include a roughening or surface finish to aid in frictional contact between the surface 112 and the surface 36, once a desired angle of articulation of the shank 4 with respect to the receiver 10 is reached.

The compression insert 14 also includes a pair of arms 114 with a U-shaped surface or saddle 116 formed therebetween. The saddle 116 defines a U-shaped channel that communicates with the bore defined by the cylindrical surface 110 and the spherical surface 112. The curved surface or saddle 116 is sized and shaped to closely receive the cylindrical rod 21. With reference to the axis D, the saddle 116 extends from top surfaces 118 of the arms to a curved lower seat 120 near a bottom surface 122 of the insert 114. In operation, the lower seat 120 (as well as a substantial portion of a remainder of the saddle 116) frictionally engages the surface 22 of the rod 21.

A base having an outer cylindrical surface 124 is disposed between the saddle 116 and the bottom surface 122. The cylindrical surface 124 also extends about the arms 114. Formed in the surface 124 and located centrally with respect to each arm 114 outer cylindrical surface is a shallow groove 126 having a substantially flat surface. The grooves 126 are sized and shaped to cooperate with the tabs 76 of the receiver 10 as will be described in greater detail below. Thus, although the grooves 126 may be of any shape, they are preferably elongate with the flat surface running parallel to the axis D and having a width that receives the respective tab 76. The bottom surface 122 is substantially planar and annular and disposed perpendicular to the axis D.

The compression or pressure insert 14 ultimately seats exclusively on the shank upper portion 8 and is disposed substantially in the upper cylindrical portion 86 of the cavity 82, with the tabs 76 engaging the insert 14 at the grooves 126, thereby holding the insert 14 in desired alignment with respect to the rod 21 as will be described in greater detail below. In operation, the insert 14 extends at least partially into the channel 66 such that the saddle 116 surface substantially contacts and engages the outer surface 22 of the rod 21 when such rod is placed in the receiver 10 and the closure structure or top 18 is tightened therein.

With reference to FIGS. 1 and 10, the closure structure or closure top 18 can be any of a variety of different types of closure structures for use in conjunction with the present invention with suitable mating structure on the upstanding arms 62. In the embodiment shown, the closure top 18 is rotatably received between the spaced arms 62, but could be a turn-cam, slide-in or other type of closure structure. The illustrated closure structure 18 is substantially cylindrical and includes an outer helically wound guide and advancement structure 132 in the form of a flange form that operably joins with the guide and advancement structure 72 disposed on the arms 62 of the receiver 10. The flange form utilized in accordance with the present invention may take a variety of forms, including those described in Applicant's U.S. Pat. No. 6,726, 689, which is incorporated herein by reference. It is also foreseen that according to the invention the closure structure guide and advancement structure could alternatively be a buttress thread, a square thread, a reverse angle thread or other thread like or non-thread like helically wound advancement structure for operably guiding under rotation and advancing the closure structure 18 downward between the arms 62 and having such a nature as to resist splaying of the arms 62 when the closure structure 18 is advanced into the U-shaped channel 66. The illustrated closure structure 18 also includes a top surface 134 with an internal drive 136 in the form of an aperture that may be a hex drive, or as illustrated, a star-shaped internal drive, for example, sold under the trademark TORX or other internal drives such as slotted, tri-wing, spanner, two or more apertures of various shapes, and the like. A driving tool (not shown) sized and shaped for engagement with the internal drive 136 is used for both rotatable engagement and, if needed, disengagement of the closure 18 from the receiver arms 62. It is also foreseen that the closure structure 18 may alternatively include a break-off head designed to allow such a head to break from a base of the closure at a preselected torque, for example, 70 to 140 inch pounds. Such a closure structure would also include a base having an internal drive to be used for closure removal. A bottom surface 138 of the closure may be planar or include a point, points, a rim or roughening for engagement with the surface 22 of the rod 21. The closure top 18 may further include a cannulation through bore extending along a central axis thereof and through the top surface 134 and the bottom surface 138. Such a through bore provides a passage through the closure 18 interior for a length of wire (not shown) inserted therein to provide a guide for insertion of the closure top into the receiver arms 62.

The elongate rod or longitudinal member 21 that is utilized with the assembly 1 can be any of a variety of implants utilized in reconstructive spinal surgery, but is normally a cylindrical elongate structure having the illustrated cylindrical surface 22 of uniform diameter and having a generally smooth surface. Although a cylindrical rod is shown, a variety of shapes are possible, including but not limited to bars of square or rectangular cross section, oval cross-section, and the like. Furthermore, the rod 21 may be a component of a dynamic stabilization connecting member, with the rod or rod portion 21 that is operatively disposed within the U-shaped channel 66 also being integral or otherwise fixed to a more flexible, bendable or damping component that extends between adjacent pairs of bone screw assemblies 1. Such a rod or rod component may be made from a variety of materials including metal, metal alloys or other suitable materials, including, but not limited to plastic polymers such as polyetheretherketone (PEEK), ultra-high-molecular weight-polyethylene (UHMWP), polyurethanes and composites, including composites containing carbon fiber. Also, the connecting component can be a polyethylene-like cord that can be tensioned.

With particular reference to FIG. 5, prior to the polyaxial bone screw assembly 1 being placed in use according to the invention, the tip 28 of the shank 6 is inserted into the through bore 95 of the retainer structure 12 and the structure 12 is moved or threaded up the shaft 6 of the shank 4 to a position about the neck 26 near the shank upper portion 8. The gap 105 between the surfaces 106 and 107 allows for such movement and the surfaces 106 and 107 may be pulled away from one another to provide clearance about the shank thread 24, if necessary. Alternatively, in some embodiments, the surfaces 106 and 107 may be moved or pulled away from one another, widening the gap 105 and allowing the retainer 12 to be slipped over and around the shank 4 at the neck 26. With reference to FIG. 6, the retainer structure 12 is then squeezed with the surfaces 106 and 107 being moved close together and a width and outer circumference of the retainer 12 being compressed to allow for bottom loading of the compressed retainer 12 and the shank upper portion 8 into the receiver 10 through the bore 90 defined by the neck 88. As the shank upper portion 8 is inserted into the cavity 82 toward the U-shaped channel 66 and is slid along the cylindrical surface 86, the spring tabs 76 are moved outwardly away from the axis A by the curved or radiused upper surface 36 of the shank upper portion 8. The outer cylindrical surface portion 35 presses against the spring tabs 76, keeping the tabs in an out-of-the-way position during assembly of the shank upper portion 8 with the retainer structure 12.

With reference to FIG. 7, the retainer structure 12, now disposed in the receiver 10 is released from compression, allowing the gap 105 to return to an original width shown in FIG. 1. The retainer structure 12 is then seated within the receiver 10 with the outer spherical surface 103 in sliding engagement with the receiver inner spherical seating surface 84. The rib 40 of the shank upper portion 8 is then coaxially aligned with the gap 105 of the retainer structure 12 and the shank body 6 is pulled downwardly away from the U-shaped channel 66 so that the rib 40 is received into the gap 105 and slidingly moved along the axes A and C between the side surfaces 106 and 107 of the retainer structure 12 until the seating surface 101 abuts the seating surface 34. At that time the conical surface portion 33 of the shank upper portion 8 is received within the inner conical surface 100 of the retainer 12 and a portion of the cylindrical surface portion 35 of the shank upper portion 8 is received within the inner cylindrical surface 99 of the retainer 12. As illustrated in FIG. 8, when the seating surfaces 101 and 34 engage, the outer spherical surface 56 of the rib 40 is flush with the outer spherical surface 103 of the retainer structure 12 and the bevels 58 and 104 also are flush. Also as illustrated in FIG. 8, the rib 40 is sized and shaped such that the side surface 54 frictionally engages the side surface 106 of the retainer structure 12 and the side surface 55 frictionally engages the side surface 107 of the retainer structure 12. As the shank upper portion 8 is pulled downwardly into the retainer 12 and into the cavity or chamber 82, the spring tabs 76 return to a position with the lower ends 80 extending toward the axis B.

Preferably, the shank 4 and or the retainer 12 are aligned and engaged to a fully frictionally mated position at a factory setting that includes tooling for holding and precise alignment until locking frictional engagement therebetween is accomplished. Permanent, rigid engagement of the shank upper portion 8 to the retainer structure 12 may be further supported by the use of adhesive, a spot weld, a deformation, or the like. At this time the shank 4 and the attached retainer 12 are fixed or coupled to one another and both are in pivotal swivelable engagement with respect to the receiver 10. The retainer 12 is in slidable engagement with the receiver curvate seating surface 84. The shank body 6 can be rotated through a substantial angular rotation relative to the receiver 10, both from side to side and from front to rear so as to substantially provide a universal or ball joint. The radiused or curved surface 36 of the shank upper portion 8 is also sized and shaped to clear a juncture between the cylindrical surface 86 and the spherical seating surface 84, if a more extreme angular position is desired.

The compression or pressure insert 14 is then inserted or top loaded into the upper opening 67 of the U-shaped channel 66 of the receiver 10 with the bottom surface 122 facing the top surface 38 of the shank upper portion 8 and the arms 118 aligned with the arms 62 of the receiver 10 as illustrated in FIG. 8. As the insert 14 is moved downwardly toward the cylindrical portion 86, the tabs 76 are received in respective grooves 126. The tabs 76 press against the insert 14 at the grooves 126, allowing for some upward and downward adjustment of the insert 14. However, rotation of the insert 14 about the receiver axis B is prohibited by the tabs 76 abutting against cylindrical surfaces of the arms 114. Surfaces defining the lower curved portion of the grooves 126 also prohibit the tabs 76 from sliding along the outer cylindrical surface of the base 124, thus resisting upward movement of the insert 14 out of the receiver 10. As illustrated in FIG. 10, the insert 14 seats on the shank upper portion 8 with the surface 112 in sliding engagement with the surface 36. The shank body 6 can still be rotated through a substantial angular rotation relative to the receiver 10, both from side to side and from front to rear so as to substantially provide a universal or ball joint, during which the insert 14 remains spaced from the retainer structure 12.

In use, the assembly 1 is typically screwed into a bone, such as a vertebra (not shown), by rotation of the shank 4 using a driving tool (not shown) that operably drives and rotates the shank 4 by engagement thereof with the tool engagement structure 42. The vertebra (not shown) may be pre-drilled to minimize stressing the bone and have a guide wire (not shown) that is shaped for the cannula 44 inserted to provide a guide for the placement and angle of the shank 4 with respect to the vertebra. A further tap hole may be made using a tap with the guide wire as a guide. Then, the assembly 1 is threaded onto the guide wire utilizing the cannulation bore 44 by first threading the wire into the bottom opening 46 and then out of the top at the internal drive 42. The shank 4 is then driven into the vertebra, using the wire as a placement guide.

With reference to FIG. 10, the rod 21 is eventually positioned in an open or percutaneous manner within the receiver U-shaped channel 66, and the closure structure or top 18 is then inserted into and advanced between the arms 62 so as to bias or push against the rod 21. Alignment of the rod surface 22 with the saddle 116 of the insert 14 is initially provided and then maintained by pressure placed at the insert grooves 126 by the tabs 76. The closure structure 18 is rotated, using a tool engaged with the inner drive 136 until a selected pressure is reached at which point the rod 21 engages the saddle 116 and the rod is urged toward, but not in contact with the lower seat 68 of the receiver 10 that defines the U-shaped channel 66. For example, about 80 to about 120 inch pounds pressure may be required for fixing the bone screw shank 6 with respect to the receiver 10.

As the closure structure 18 rotates and moves downwardly into the receiver 10, the bottom surface 138 presses against the rod surface 22, biasing the rod into engagement with the compression insert 14 that operably produces a frictional engagement between the insert surface 112 and the shank surface 36, urging the shank upper portion 8 and attached retainer 12 in a direction toward the base 60 of the receiver 10, so as to frictionally seat the spherical surface 103 of the retainer 12 against the inner spherical surface 84 of the receiver 10, also fixing the shank 4 and the retainer 12 in a selected, rigid position relative to the receiver 10. At this time it is also possible for the retainer 12 to expand somewhat for an even tighter fit in the receiver cavity lower seat 84. This is especially so if the gap in the retainer is somewhat tapered or wedged in shape. However, the retainer 12 does not come into contact with the insert 14, the insert 14 being exclusively seated on and pressing upon the shank upper portion 8 in any and all articulated positions of the shank 4 with respect to the receiver 10. The retainer structure 12 that is spaced from the insert 14 engages only the shank upper portion 8 and the receiver 10; the structure 12 being pressed upon by the upper portion 8 and in turn pressing upon the receiver 10 inner seating surface.

If removal of the rod 21 from any of the bone screw assemblies 1 is necessary, or if it is desired to release the rod 21 at a particular location, disassembly is accomplished by using the driving tool (not shown) that mates with the internal drive 136 on the closure structure 18 to rotate and remove the closure structure 18 from the cooperating receiver 10. Disassembly is then accomplished in reverse order to the procedure described previously herein for assembly.

Figure 11:
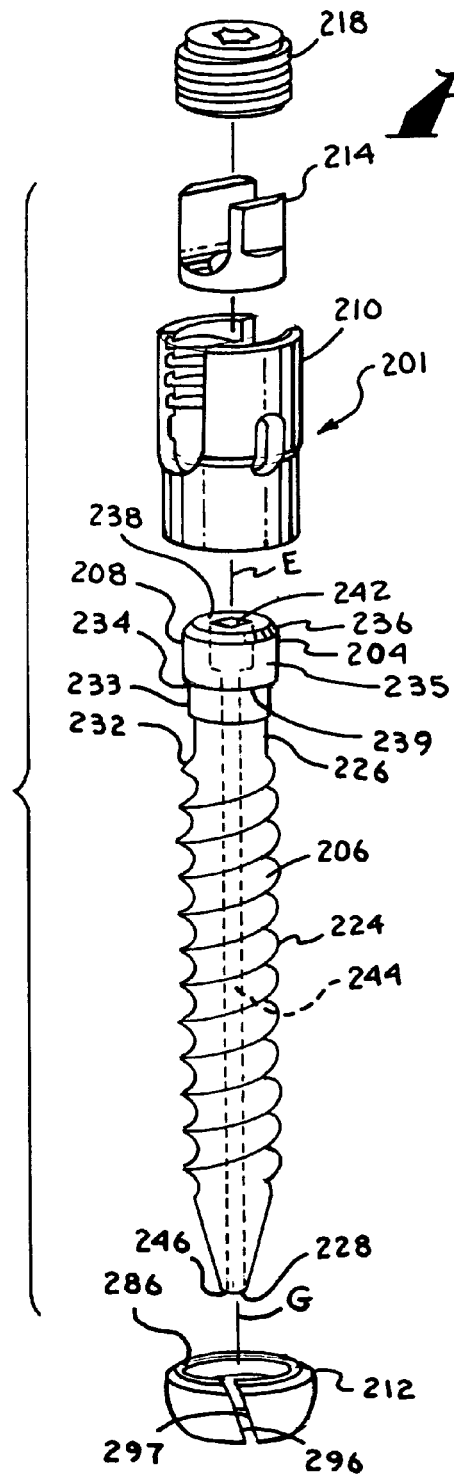
FIG. 11 is an exploded perspective view of a second embodiment of a polyaxial bone screw assembly according to the present invention having a shank, a receiver, a retainer and a compression insert and further shown with a closure structure.
Figure 12:
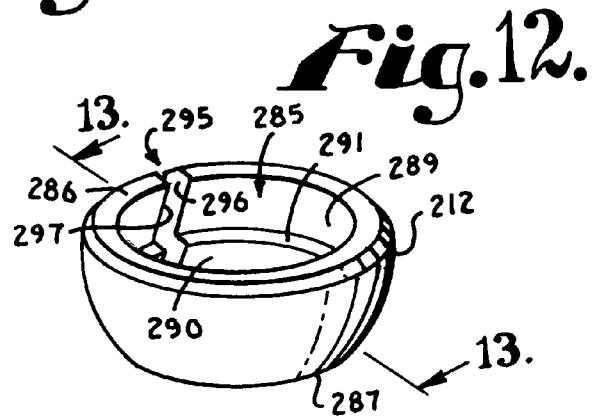
FIG. 12 is an enlarged perspective view of the retainer of FIG. 11.
Figure 13:
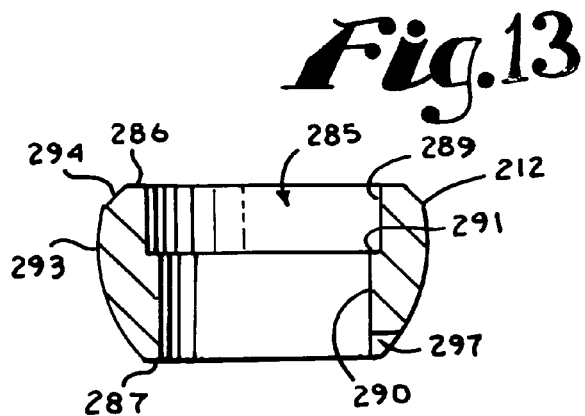
FIG. 13 is an enlarged cross-sectional view taken along the line 13-13 of FIG. 12.

With reference to FIGS. 11-14, an alternative bone screw assembly of the invention, generally 201 includes a shank 204 that further includes a body 206 integral with an upper portion or capture structure 208; a head or receiver 210; a retainer 212 illustrated as an open retaining and articulating structure; and a compression insert 214. With reference to FIGS. 11 and 14, the assembly 201 cooperates with a closure structure 218 and a rod 221. The receiver 210, the compression insert 214, the closure structure 218 and the rod 221 are identical or substantially similar to the respective receiver 10, insert 14, closure structure 18 and rod 21 previously described herein with respect to the assembly 1.

The shank 204 is substantially similar to the shank 4 previously described herein with the exception that the shank 204 does not include a rib or fin similar to the rib 40 of the shank upper portion 8 and the conical surface 33 is replaced by a cylindrical surface 233. The shank 204 is elongate, with the shank body 206 having a helically wound bone implantable thread 224 extending from near a neck 226 located adjacent to the upper portion 208 to a tip 228 of the body 206 and extending radially outwardly therefrom. During use, the body 206 utilizing the thread 224 for gripping and advancement is implanted into the vertebra (not shown) leading with the tip 228 and driven down into the vertebra with an installation or driving tool, so as to be implanted in the vertebra to near the neck 226, and as is described more fully in the paragraphs below. The shank 204 has an elongate axis of rotation generally identified by the reference letter E.

The neck 226 extends axially upwardly from the shank body 206. The neck 226 may be of reduced radius as compared to an adjacent top 232 of the threaded body 206. Further extending axially upwardly from the neck 226 is the shank upper portion 208 that provides a connective or capture apparatus disposed at a distance from the threaded body top 232 and thus at a distance from the vertebra when the body 206 is implanted in the vertebra. To provide a biologically active interface with the bone, the threaded shank body 206 may be coated, perforated, made porous or otherwise treated as previously described herein with respect to the shank body 6.

The shank upper portion 208 is configured for a polyaxial connection between the shank 204 and the receiver 210 and capturing the shank 204 upper portion 208 in the receiver 210. The upper portion 208 generally includes the first, lower or in-set cylindrical surface portion 233 located adjacent the neck 226; an annular planar retainer seat portion 234; an off- or out-set substantially cylindrical second surface portion 235; a curved and annular upper surface 236 and a planar top surface 238. The planar top surface 238 is substantially perpendicular to the cylindrical surface portion 235 and substantially parallel to the seat portion 234. The cylindrical portion 233 extends between the neck 26 and the retainer seat 34. The retainer seat 234 defines a lower edge 239 of the cylindrical portion 235. A tool engagement internal drive feature or structure 242 is formed in the top end surface 238. A driving tool (not shown) has a driving projection configured to fit within the tool engagement structure 242 for both driving and rotating the shank body 206 into the vertebra.

The upper surface 236 of the shank 204 is preferably curved or radiused as shown in the drawings, for exclusive contact engagement or positive mating engagement with the compression insert 214, when the bone screw assembly 201 is assembled, as shown in FIG. 14 and in any alignment of the shank 204 relative to the receiver 210. The illustrated surface 236 also has approximately the same radius as an inner spherical seating surface of the receiver 210, allowing for clearance of the shank 204 with respect to the receiver 210 and thus a desired degree and magnitude of articulation of the shank 204 with respect to the receiver 210. In certain embodiments, the surface 236 is smooth. While not required in accordance with the practice of the invention, the surface 236 may be scored or knurled to further increase frictional positive mating engagement between the surface 236 and the compression insert 214.

The shank 204 shown in the drawings is cannulated, having a small central bore 244 extending an entire length of the shank 204 along the axis E. The bore 244 is defined by an inner cylindrical wall of the shank 204 and has a circular opening 246 at the shank tip 228 and an upper opening communicating with the internal drive 242. The bore 244 is coaxial with the threaded body 206 and the upper portion 208. The bore 244 provides a passage through the shank 204 interior for a length of wire (not shown) inserted into the vertebra (not shown) prior to the insertion of the shank body 206, the wire providing a guide for insertion of the shank body 206 into the vertebra (not shown). The retainer seat 234 of the shank upper portion 208 is a substantially planar annular surface disposed perpendicular to the Axis E of the shank and sized and shaped to engage the retainer structure 212 as will be described in greater detail below. The first or inner cylindrical surface portion 233 and the second or outer cylindrical surface portion 235 are also sized and shaped to slidingly engage portions of the retainer structure 212, also described in greater detail subsequently herein.

The retainer structure or open ring 212 is used to capture the shank upper portion 208 and retain the upper portion 208 within the receiver 210. The retainer 212, best illustrated in FIGS. 12 and 13, has an operational central axis that is the same as the rotational axis E associated with the shank 204, but when the retainer structure 212 is separated from the shank 204, the axis of rotation is identified as axis G. The retainer structure 212 has a central bore, generally 285, that passes entirely through the retainer structure 212 from a top surface 286 to a bottom surface 287 thereof. Both the top surface 286 and the bottom surface 287 are substantially planar and disposed perpendicular to the axis G. An inner discontinuous and substantially cylindrical surface 289 defines a substantial portion of the bore 285. The cylindrical surface 289 is sized and shaped to be slidingly received and frictionally engaged about a lower segment of the cylindrical surface portion 235 of the shank upper portion 208. An inner discontinuous substantially cylindrical surface 290 also defines a substantial portion of the bore 285. The cylindrical surface 290 is sized and shaped to be slidingly received and frictionally engaged about the in-set or inner cylindrical surface portion 233 of the shank upper portion 208. A discontinuous and substantially planar annular seating surface 291 is disposed between and connects the surface 289 with the surface 290. The seating surface 291 is disposed substantially perpendicular to the axis G. The seating surface 291 is sized and shaped to abut against and frictionally engage the seating surface 234 of the shank upper portion 208. The cooperating cylindrical surfaces 289 and 235; cylindrical surfaces 290 and 233; and planar annular abutting seating surfaces 291 and 234 cooperate to prohibit the retainer structure 212 from sliding in a direction upwardly off of the upper portion 208 toward a U-shaped channel of the receiver 210. It is foreseen a shank upper portion and retainer structure combination according to the invention may alternatively include cooperating conical surfaces or a conical surface cooperating with a cylindrical surface and cooperating abutting or seat surfaces adjacent to planar or other shaped surfaces in lieu of or in addition to the illustrated cooperating cylindrical surfaces. It is also foreseen that shank upper portion and retainer structure combinations according to the invention may include cooperating conical or cylindrical surfaces and not include the illustrated abutting annular surfaces 234 and 291.

The retainer structure 212 further includes a discontinuous curvate outer surface 293 and a discontinuous bevel 294 disposed between the outer surface 293 and the top surface 286.

A gap or slit, generally 295 is defined by and disposed between facing side surfaces 296 and 297. The side surface 296 and 297, in the embodiment shown, are substantially parallel and evenly spaced from one another and are disposed at an oblique angle with respect to the top surface 286 and the bottom surface 287, but other configurations are possible. The gap or slit 295 allows for the somewhat flexible and resilient retainer structure 212 to be squeezed or otherwise manipulated by moving the surfaces 296 and 297 toward or away from one another and in opposite directions with reference to the axis G. The resilient nature of the structure 212 allows for the structure 212 to spring back into an original shape as shown in FIGS. 11 and 14 after being manipulated. As will be described in greater detail below, the oblique orientation of the surfaces 296 and 297 allows for a desired narrow gap or slit 295 to be sufficient for bottom loading of the structure 212 as the surfaces 296 and 297 slide against each other when the structure 212 is squeezed, for example, the surface 296 moving upwardly and the surface 297 moving downwardly or oppositely with respect to the axis G. Thus, such oblique orientation of the surfaces 296 and 297 provides for sufficient minimizing of a width or circumference of the structure 212 for bottom loading into the receiver 210 and also provides almost full coverage of the structure 212 about the shank upper portion 208 when the structure 212 is engaged with the portion 208 and operatively disposed within the receiver 210. Again, it is foreseen that in other embodiments according to the invention, the surfaces 296 and 297 may be disposed at other oblique angles or alternatively substantially perpendicular to the top and bottom surfaces 286 and 287. In such an alternative embodiment, a gap between the surfaces 296 and 297 may be wider than the illustrated gap 285.

The retainer structure 212 radially outer substantially spherically shaped surface 293 is sized and shaped to mate with the spherically shaped inner seating surface of the receiver 210 that is identical or substantially similar to the inner receiving surface 84 of the receiver 10 previously described herein with respect to the assembly 1. When in a non-compressed state, a radius of the surface 293 is larger than the radius of a lower neck 288 of the receiver 210. The shank upper portion 208 cylindrical surface 233, annular seat 234 and cylindrical surface 235, when engaged with the retainer 212, fix the retainer 212 at a desired diameter or width such that the retainer 212 is prohibited from moving downwardly through the lower neck 288 and out of the receiver 210. Although not required, it is foreseen that the outer curvate shaped surface 293 may be a high friction surface such as a knurled surface or the like.

With particular reference to FIG. 11, prior to the polyaxial bone screw assembly 201 being placed in use according to the invention, the tip 228 of the shank 206 is inserted into the through bore 285 of the retainer structure 212 and the structure 212 is moved or threaded up the shaft 206 of the shank 204 to a position about the neck 226 near the shank upper portion 208. The gap 295 between the surfaces 296 and 297 allows for such movement and the surfaces 296 and 297 may be pulled away from one another to provide clearance about the shank thread 224, if necessary. Alternatively, in some embodiments, the surfaces 296 and 297 may be moved or pulled away from one another, widening the gap 295 and allowing the retainer 212 to be slipped over and around the shank 204 at the neck 226. The retainer structure 212 is then squeezed with the surfaces 296 and 297 moved into engagement with one another and the structure being slightly twisted to slide the surfaces 296 and 297 in opposite directions with respect to the axis G and thus the top surface 286 and the bottom surface 287 slightly contorted into a non-planar orientation to result in a width or outer circumference of the structure 212 small enough to enter the receiver 210 through the lower restrictive neck 288. Such contorted and squeezed orientation of the structure 212 about the shank neck 226 allows for bottom loading of the compressed retainer 212 and the shank upper portion 208 into the receiver 210 through a bore defined by the neck 288. The retainer structure 212, now disposed in the receiver 210 is released from compression, allowing the slit or gap 295 to return to an original width and orientation shown in FIGS. 11 and 14. The retainer structure 212 is then seated within the receiver 210 with the outer spherical surface 293 in sliding engagement with an inner spherical seating surface of the receiver 210. The shank body 206 is pulled downwardly toward the lower neck 288 and along the axes E and G until the seating surface 291 abuts the seating surface 234. At that time the cylindrical surface portion 233 of the shank upper portion 208 is received within the inner cylindrical surface 290 of the retainer 212 and a portion of the cylindrical surface portion 235 of the shank upper portion 208 is received within the inner cylindrical surface 289 of the retainer 212. Permanent, rigid engagement of the capture structure 208 to the retainer structure 212 may be further supported by the use of adhesive, a spot weld, a deformation, or the like. At this time the shank 204 and the attached retainer 212 are fixed to one another and both are in swivelable engagement with respect to the receiver 210. The shank body 206 can be rotated or swivelled through a substantial angular rotation relative to the receiver 210, both from side to side and from front to rear so as to substantially provide a universal or ball joint.

The compression or pressure insert 214 is then inserted or top loaded into the receiver 210 in a manner identical or similar to that described previously herein with respect to the insert 14 and the receiver 10. As with the insert 14, the insert 214 remains spaced from the retainer structure 212 as the shank body 206 is swivelled through a substantial angular rotation relative to the receiver 210, both from side to side and from front to rear. With reference to FIG. 14, in use, the assembly 201 is typically implanted with a cooperating longitudinal connecting member, such as the rod 221, as previously described herein with respect to the assembly 1. The assembly 201 may also be disassembled as previously described herein with respect to the assembly 1.

It is to be understood that while certain forms of the present invention have been illustrated and described herein, it is not to be limited to the specific forms or arrangement of parts described and shown.

What is claimed and desired to be secured by Letters Patent is as follows:

1. A polyaxial bone anchor comprising:
a) a shank having a body for fixation to a bone and an upper portion, the body and upper portion being generally aligned along an axis of rotation thereof, the upper portion having an upper surface, a first section and a second section, the first section being adjacent the upper surface, the first section having a first width measured perpendicular to the axis, the second section having a second width measured perpendicular to the axis, the second width being different than the first width, the second section being disposed between the body and the first section;
b) a receiver having a top portion and a base, the receiver top portion defining an open channel, the base having a seating surface partially defining a cavity, the channel communicating with the cavity, the cavity communicating with an exterior of the base through an opening sized and shaped to receive the shank upper portion therethrough;
c) a compression insert disposed in the receiver, the insert having a mating surface exclusively frictionally engageable with the upper surface of the shank upper portion; and
d) a retainer having a through slit and an internal surface sized and shaped to closely receive the shank upper portion at the second section, the shank upper portion and the retainer being in non-swivelable relation to one another, both the upper portion and the retainer being in swivelable relation within the receiver, providing selective angular positioning of the shank with respect to the receiver, the retainer being in slidable engagement with the receiver seating surface, the retainer being substantially spaced from the compression insert at any and all angular positions of the shank with respect to the receiver; and
e) a resilient structure extending from the receiver and biasing against the compression insert at a depression formed in a surface of the insert, the resilient structure prohibiting rotational movement of the compression insert within the receiver; and wherein
f) the resilient structure is a pair of opposed spring tabs attached to the receiver and extending toward a central axis of the receiver.

2. A polyaxial bone anchor comprising:
a) a shank having a body for fixation to a bone and an upper portion, the body and upper portion being generally aligned along an axis of rotation thereof, the upper portion having an upper surface, a first section and a second section, the first section being adjacent the upper surface, the first section having a first width measured perpendicular to the axis, the second section having a second width measured perpendicular to the axis, the second width being different than the first width, the second section being disposed between the body and the first section;
b) a receiver having a top portion and a base, the receiver top portion defining an open channel, the base having a seating surface partially defining a cavity, the channel communicating with the cavity, the cavity communicating with an exterior of the base through an opening sized and shaped to receive the shank upper portion therethrough;
c) a compression insert disposed in the receiver, the insert having a mating surface exclusively frictionally engageable with the upper surface of the shank upper portion; and
d) a retainer having a through slit and an internal surface sized and shaped to closely receive the shank upper portion at the second section, the shank upper portion and the retainer being in non-swivelable relation to one another, both the upper portion and the retainer being in swivelable relation within the receiver, providing selective angular positioning of the shank with respect to the receiver, the retainer being in slidable engagement with the receiver seating surface, the retainer being substantially spaced from the compression insert at any and all angular positions of the shank with respect to the receiver; and
e) a protruding structure extending from the receiver and engageable with a surface of the insert, the structure prohibiting rotational movement of the compression insert within the receiver; and wherein
f) the protruding structure is a pair of opposed protrusions attached to the receiver and extending toward a central axis of the receiver.

* * * * *